(12) United States Patent
Wang et al.

(10) Patent No.: US 7,983,458 B2
(45) Date of Patent: Jul. 19, 2011

(54) IN VIVO AUTONOMOUS CAMERA WITH ON-BOARD DATA STORAGE OR DIGITAL WIRELESS TRANSMISSION IN REGULATORY APPROVED BAND

(75) Inventors: Kang-Huai Wang, Saratoga, CA (US); Gordon Wilson, San Francisco, CA (US)

(73) Assignee: Capso Vision, Inc., Saratoga, CA (US)

( * ) Notice: Subject to any disclaimer, the term of this patent is extended or adjusted under 35 U.S.C. 154(b) by 1162 days.

(21) Appl. No.: 11/533,304

(22) Filed: Sep. 19, 2006

(65) Prior Publication Data
US 2007/0098379 A1    May 3, 2007

Related U.S. Application Data

(60) Provisional application No. 60/760,794, filed on Jan. 19, 2006, provisional application No. 60/760,079, filed on Jan. 18, 2006, provisional application No. 60/739,162, filed on Nov. 23, 2005, provisional application No. 60/730,797, filed on Oct. 26, 2005, provisional application No. 60/719,135, filed on Sep. 20, 2005.

(51) Int. Cl.
*G06K 9/00* (2006.01)
(52) U.S. Cl. ......... 382/128; 382/236; 348/699; 348/700
(58) Field of Classification Search ................... 382/128
See application file for complete search history.

(56) References Cited

U.S. PATENT DOCUMENTS

| | | | |
|---|---|---|---|
| 4,270,077 A | 5/1981 | Swartz | |
| 5,581,302 A * | 12/1996 | Ran et al. | 375/240.16 |
| 5,588,067 A * | 12/1996 | Peterson et al. | 382/103 |
| 5,604,531 A | 2/1997 | Iddan | |
| 6,161,031 A | 12/2000 | Hochman et al. | |
| 6,428,469 B1 | 8/2002 | Iddan | |
| 6,466,618 B1 * | 10/2002 | Messing et al. | 375/240.01 |
| 6,480,225 B1 * | 11/2002 | Kim | 348/143 |
| 6,709,387 B1 * | 3/2004 | Glukhovsky et al. | 600/109 |
| 6,800,060 B2 * | 10/2004 | Marshall | 600/309 |
| 6,803,945 B1 * | 10/2004 | Needham | 348/207.1 |

(Continued)

FOREIGN PATENT DOCUMENTS

EP    1 492 352    12/2004
(Continued)

OTHER PUBLICATIONS

Supplementary European Search Report for EP 06 85 1316, dated Jun. 18, 2010, 8 pages.

(Continued)

*Primary Examiner* — Sath V. Perungavoor
(74) *Attorney, Agent, or Firm* — Edward C. Kwok; Haynes and Boone, LLP

(57) ABSTRACT

A capsule camera apparatus includes a swallowable housing, a light source within the housing, a camera within the housing for capturing a first digital image and a second digital image of a view of the camera illuminated by the light source, a a motion detector that detects a motion of the housing the first digital image and the second digital image, and a motion evaluator that selects a disposition of the second digital image, based on a metric on the motion. The disposition may include writing the second image into an archival storage or providing the second digital image to the outside by a wireless communication link.

81 Claims, 17 Drawing Sheets

U.S. PATENT DOCUMENTS

| | | | |
|---|---|---|---|
| 6,936,003 B2* | 8/2005 | Iddan | 600/114 |
| 6,939,292 B2* | 9/2005 | Mizuno | 600/118 |
| 7,153,259 B2* | 12/2006 | Matsuzawa et al. | 600/160 |
| 7,271,830 B2* | 9/2007 | Robins et al. | 348/208.6 |
| 7,492,935 B2* | 2/2009 | Glukhovsky | 382/128 |
| 7,643,056 B2* | 1/2010 | Silsby | 348/155 |
| 2003/0023150 A1* | 1/2003 | Yokoi et al. | 600/300 |
| 2003/0202605 A1* | 10/2003 | Hazra et al. | 375/240.26 |
| 2005/0025368 A1* | 2/2005 | Glukhovsky | 382/236 |
| 2005/0058701 A1 | 3/2005 | Gross et al. | |
| 2005/0143624 A1* | 6/2005 | Iddan | 600/112 |
| 2005/0183733 A1 | 8/2005 | Kawano | |
| 2005/0207664 A1 | 9/2005 | Ramasastry et al. | |
| 2006/0293558 A1* | 12/2006 | De Groen et al. | 600/101 |
| 2007/0098379 A1* | 5/2007 | Wang et al. | 396/14 |
| 2007/0116119 A1* | 5/2007 | Wang | 375/240.12 |
| 2009/0299359 A1* | 12/2009 | Swain | 606/27 |
| 2009/0322865 A1* | 12/2009 | Wang et al. | 348/68 |

FOREIGN PATENT DOCUMENTS

| | | |
|---|---|---|
| WO | 2004/088448 | 10/2004 |

OTHER PUBLICATIONS

Okubo et al. "Video Codec Standardization in CCITT Study Group XV" Signal Processing. Image Communication, Elsevier Science Publishers, Amsterdam, NL, Jun. 1, 1989, pp. 45-54.

European Examination Report for EP 06 85 1316, dated Jan. 20, 2011, 5 pages.

Yeh et al. "Buffer Size Optimization for Full-Search Block Matching Algorithms," IEEE Computer Soc., Jul. 14-16, 2007, pp. 76-85.

* cited by examiner

IN VIVO AUTONOMOUS CAMERA WITH ON-BOARD DATA STORAGE OR DIGITAL WIRELESS TRANSMISSION IN REGULATORY APPROVED BAND

CROSS-REFERENCES TO RELATED APPLICATIONS

The present invention is related to and claims priority to (1) U.S. Provisional Patent Application, entitled "In Vivo Autonomous Sensor with On-Board Data Storage," Ser. No. 60/719,135, filed on Sep. 20, 2005; (2) U.S. Provisional Patent Application, entitled "InVivo Autonomous Sensor with On-Board Data Storage," Ser. No. 60/730,797, filed on Oct. 26, 2005; (3) U.S. Provisional Patent Application, entitled "InVivo Autonomous Sensor with On-Board Data Storage," Ser. No. 60/739,162, filed on Nov. 23, 2005; (4) U.S. Provisional Patent Application, entitled "InVivo Autonomous Sensor with Panoramic Camera," Ser. No. 60/760,079, filed on Jan. 18, 2006; and (5) U.S. Provisional Patent Application, entitled "InVivo Autonomous Sensor with On-Board Data Storage," Ser. No. 60/760,794, filed on Jan. 19, 2006. These U.S. Provisional Patent Applications are hereby incorporated by reference in their entireties.

BACKGROUND OF THE INVENTION

1. Field of the Invention

The present invention relates to diagnostic imaging inside the human body. In particular, the present invention relates to obtaining images of the digestive tract using capsule endoscopy.

2. Discussion of the Related Art

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools. However, they do have a number of limitations, present risks to the patient, are invasive and uncomfortable for the patient, and their cost restricts their application as routine health-screening tools.

Because of the difficulty traversing a convoluted passage, endoscopes cannot reach the majority of the small intestine and special techniques and precautions, that add cost, are required to reach the entirety of the colon. Endoscopic risks include the possible perforation of the bodily organs traversed and complications arising from anesthesia. Moreover, a trade-off must be made between patient pain during the procedure and the health risks and post-procedural down time associated with anesthesia. Endoscopies are necessarily inpatient services that involve a significant amount of time from clinicians and thus are costly.

An alternative in vivo image sensor that addresses many of these problems is capsule endoscope. A camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An early example of a camera in a swallowable capsule is described in U.S. Pat. No. 5,604,531. Other patents, such as U.S. Pat. Nos. 6,709,387 and 6,428,469, describe more details of such a system, using a transmitter to send the camera images to an external receiver. Still other patents, including U.S. Pat. No. 4,278,077, describe similar technologies. For example, U.S. Pat. No. 4,278,077 shows a capsule with a camera for the stomach, which includes film in the camera. U.S. Pat. No. 6,939,292 shows a capsule with a buffering memory, a timer, and a transmitter.

One advantage of an autonomous encapsulated camera with an internal battery is that measurements may be made with the patient ambulatory, out of the hospital, and with moderate restriction of activity. The base station includes an antenna array surrounding the bodily region of interest and this array can be temporarily affixed to the skin or incorporated into a wearable vest. A data recorder is attached to a belt and includes a battery power supply and a data storage medium for saving recorded images and other data for subsequent uploading onto a diagnostic computer system.

A typical procedure consists of an inpatient visit in the morning during which a clinician attaches the base station apparatus to the patient and the patient swallows the capsule. The system records images beginning just prior to swallowing and records images of the gastrointestinal (GI) tract until its battery becomes fully discharged. Peristalsis propels the capsule through the GI tract. The rate of passage depends on the degree of motility. Usually, the small intestine is traversed in 4 to 8 hours. After a prescribed period, the patient returns the data recorder to the clinician who then uploads the data onto a computer for subsequent viewing and analysis. The capsule is passed in time through the rectum and need not be retrieved.

The capsule camera allows the GI tract from the esophagus down to the end of the small intestine, especially the small intestine, to be imaged in its entirety, although it is not optimized to detect anomalies in the stomach. Color photographic images are captured so that anomalies can be detected even when only small visually recognizable characteristics, not topography, are available. The procedure is pain-free and requires no anesthesia. Risks associated with the capsule passing through the body are minimal—certainly, the risk of perforation is much reduced relative to endoscopy. The cost of the procedure is also less than for an endoscopy due to the decreased use of clinician time and clinic facilities, and the absence of anesthesia.

Despite these advantages, the existing capsule camera solutions have limitations as well. Although the base station and data recorder are designed to minimize discomfort and maximize mobility, they necessarily hamper the patient during the measurement and create discomfort. Also, sleeping with the apparatus attached would be difficult, necessitating that the measurement commence and finish during waking hours. The cost of the procedure is not sufficiently low to allow the procedure to become a routine screening procedure. The time required for a clinician to attach the antenna array and the data recorder is a significant contributor to the total cost. The costs of the data recorders and the base stations become significant as the number of patients concurrently measured increases beyond one or two. Also, the radio transmitter in the capsule, which includes an antenna, is a significant contributor to its cost, size, and power consumption. The radio link, then, is responsible, directly and indirectly, for much of the cost. The wireless system may also suffer radio interference from MRI, airport security devices, amateur video systems, or other sources of RF radio signal in the spectrum. There may also be interference between this system and other implant devices, either within a single patient or between two nearby persons. Another significant factor contributing to cost is the doctor's time for viewing the images. In current devices, such images may number in many thousands, which adds to patient history archiving cost and presents an obstacle for internet transmission of such data.

Another limitation of the current solutions is their inability to reliably image the colon. The colon presents a number of challenges for the imaging system. A number of complications arise because the capsule takes longer to pass through the entire GI tract than just through the small intestine. In fact, ingested material can easily take 24 hours or longer to pass through the colon, although this time can be reduced with motility-enhancing drugs. Imaging the colon with an existing system would thus require the patient to wear the base station, including the antenna array, and the data recorder for a longer period of time.

The increased measurement time leads to logistical complications. The colon must be purged prior to imaging and remain free of digested or partially-digested food which would obscure the colon wall from the camera. Any beverages, such as fruit juices or sodas, that are metabolized by bacteria in the colon will thereupon become turbid. Thus, if an autonomous capsule taken orally is to image the colon, the patient must refrain from eating or drinking fluids (except water) for approximately a period lasting at least from the time the purgative is consumed until the time the capsule is passed (minus the minimum time taken for the digested food or beverage to reach the camera in the colon). Even with the aid of motility-enhancing drugs, the fast must persist for at least eight hours after the capsule is swallowed, as compared to just a few hours for imaging of the small intestine alone. Additional restrictions on the timing of the measurement arise from the practical requirement that the data recorder and the antenna array be attached during normal office hours and by the fact that sleeping with the apparatus attached would be difficult. All of these logistical constraints make it difficult to design a protocol which is convenient for both patients and clinicians, which minimizes the discomfort of fasting, and which maximizes the number of patients that one clinic or clinician can test.

U.S. Pat. No. 6,800,060 describes a swallowable data-recorder capsule that may be retrieved after passing from the body. However, this system specifies an expensive and rare ultra-high-density atomic-resolution storage (ARS) medium. U.S. Patent Application Publication US2005/0183733 shows a capsule with a balloon that is deployed depending on positional information.

BRIEF SUMMARY OF THE INVENTION

According to one embodiment of the present invention, a capsule camera apparatus and a method provide a swallowable housing, a light source within the housing, a camera within the housing for capturing a first digital image and a second digital image of a scene illuminated by the light source, a motion detector that detects a motion of the housing the first digital image and the second digital image, and a motion evaluator that designates one of the digital images for further processing, based on a metric on the motion. The further processing may include writing the second image into an archival storage, deleting the image or providing the second digital image to an outside receiver over a wireless communication link.

According to one embodiment of the present invention, a capsule camera apparatus and a method provide a swallowable housing, a light source within the housing, a camera within the housing for capturing digital images of a scene illuminated by the light source, and an archival storage for storing the captured images.

According to one embodiment, the archival storage device may be a semiconductor memory device, such as a flash memory device. The capsule may include an output port for accessing the archival storage device through, for example, a connector that may be provided at a feed-through on the housing. In one embodiment, the capsule is capable of receiving power from an external power source, so that the archival storage may be accessed even if the capsule's own on-board power source has been exhausted.

According to one embodiment of the present invention, the motion detection is conducted using a portion of each image, the portion being stored in a partial frame buffer. In one embodiment, two partial frame buffers are used as an operand partial frame buffer and a reference frame buffer, respectively. The reference frame buffer is the one containing a previously stored or transmitted digital image. When the image in the operand partial frame buffer is determined not to be stored, that partial frame buffer may be overwritten by the next digital image to be motion-detected. Otherwise, the operand partial frame buffer would be designated the next reference partial frame buffer, and the current reference partial frame buffer is designated the next operand partial frame buffer.

According to one embodiment of the present invention, motion detection is performed by computing, for example, motion vectors, absolute differences between the digital images, or by comparing "centers-of-mass" of the images. In each such method, a metric indicates the degree of the motion detected. Such metrics may include the number of zero motion vectors detected, a total variance from the average absolute differences or a "distance" between the centers-of-mass of the images, based on the respective intensities of the images.

According to one embodiment of the present invention, in addition to the images, the capsule camera apparatus provides one or more secondary sensors to detect additional environmental parameters, such as pH, temperature or pressure.

According to one embodiment of the present invention, in which the designated digital image is transmitted over a wireless link, a protocol encoder is provided for encoding data prior to transmission. The transmitted data is received by a base station over the wireless link. The base station may also include an interface to a workstation and an archival storage. The data stored in the archival storage may then be made available for access by the workstation. The motion detector may be provided in the base station, so that the decision to store or not to store an image in the archival system can be made at the base station. Communication between the capsule and the base station may be made bidirectional by including in the base station and the capsule each a transmitter and a receiver (i.e., a transceiver).

According to one embodiment of the present invention, compression on a digital image is accomplished using an image compression algorithm, which may provide different compression ratios for various stages of image processing, depending on how the image is intended to be use at each stage. For example, a first compression ratio is provided when the digital image is being motion-detected, and a second compression ratio is provided for storage or wireless transmission.

According to one embodiment of the present invention, a capsule camera has an on-board semiconductor memory device which stores images that are selectively taken along the GI tract. Movement detection selects only a subset of images that are captured for further processing. As a result, the apparatus of present invention requires only a small frame buffer, i.e., one that is a mere fraction of the size that was deemed necessary in the prior art.

According to another embodiment of the present invention, a capsule camera capable of digital wireless communication enables wireless transmission of images in a regulatory approved band.

BRIEF DESCRIPTION OF THE DRAWINGS

To facilitate cross-referencing among the figures, like elements in the figures are accorded like reference numerals.

DETAILED DESCRIPTION OF THE INVENTION

Today, semiconductor memories are low-cost, low-power, easily available from multiple sources, and compatible with application specific integrated circuit (ASIC) and sensor electronics (i.e., the data sources), and a personal computer (i.e., the data destination) without format conversion devices. One embodiment of the present invention allows images to be stored in an "on-board storage" using merchant semiconductor memories (i.e., "off-the-shelf" memories, or memories manufactured using industry standard memory processes, or readily available memory processes). To enable taking a large number of diagnostic images in such areas as the colon, a method of the present invention controls the number of images stored in the semiconductor memories by detecting camera movements. One embodiment of the present invention takes advantage of the fact that, for much of the time, either the capsule does not move in the GI tract, or the portion of the GI tract within the camera's view is not changing. For such periods of time, the images need not be stored.

According to another aspect of the present invention, a specialized frame buffer is provided. As a 640×480 resolution VGA-type image has 300,000 pixels, and if each such pixel is represented equally by one byte of data (e.g., 8 bits), the image requires a 2.4 M-bit frame buffer ("regular frame buffer"). Because of its physical and power constraints, in practice, a capsule camera can provide only a fraction of the regular frame buffer. One embodiment of the present invention provides, therefore, a highly efficiency image compression[1] algorithm to reduce the storage requirement, taking into consideration the limited processing power and limited memory size available in the capsule. In one embodiment, one or more "partial frame buffers" are provided, with each partial frame buffer being significantly smaller than a regular frame buffer. As the per-bit size in memory circuits continues to decrease, a method of the present invention may use the larger memory size made possible to achieve greater sensor resolution.

[1] The digital image may be compressed using a suitable lossy compression technique.

Figure 1:
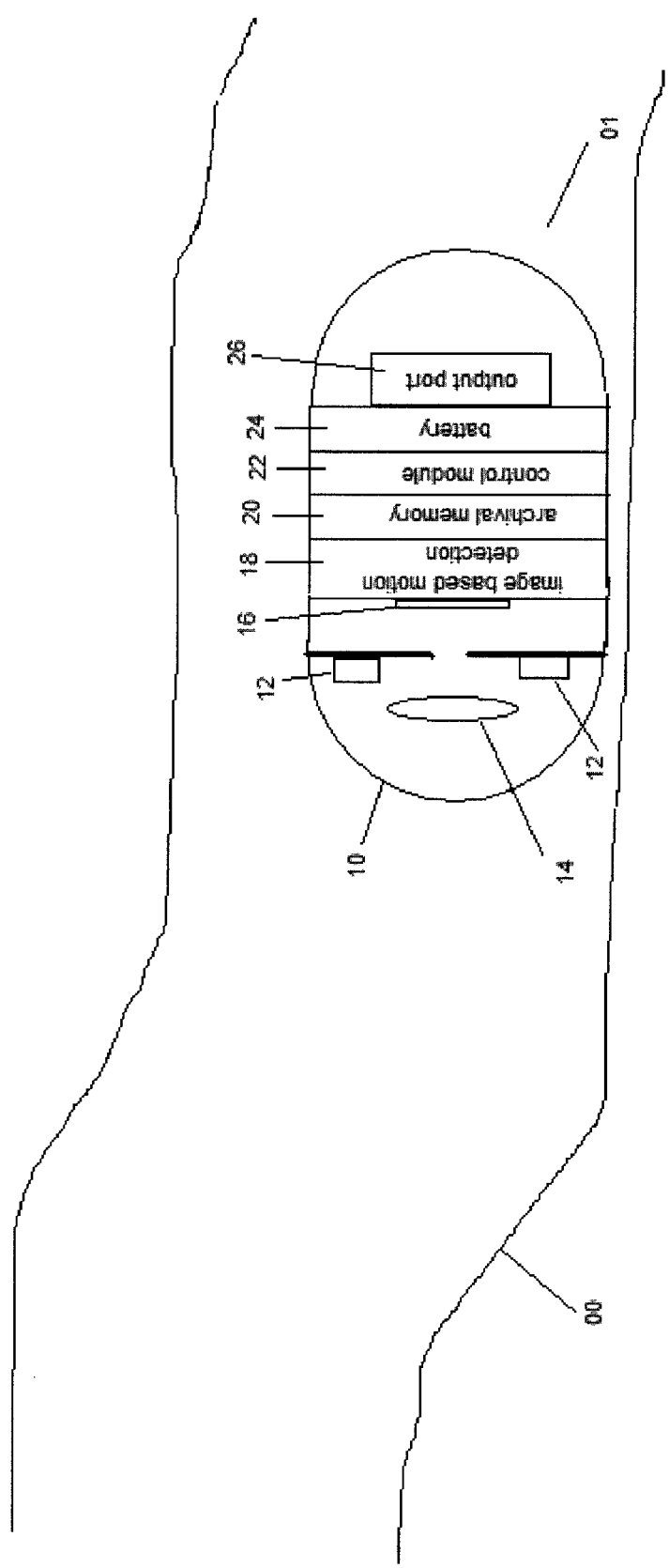
FIG. 1 shows schematically capsule system 01 in the GI tract, according to one embodiment of the present invention, showing the capsule in a body cavity.

FIG. 1 shows a swallowable capsule system 01 inside body lumen 00, in accordance with one embodiment of the present invention. Lumen 00 may be, for example, the colon, small intestines, the esophagus, or the stomach. Capsule system 01 is entirely autonomous while inside the body, with all of its elements encapsulated in a capsule housing 10 that provides a moisture barrier, protecting the internal components from bodily fluids. Capsule housing 10 is transparent, so as to allow light from the light-emitting diodes (LEDs) of illuminating system 12 to pass through the wall of capsule housing 10 to the lumen 00 walls, and to allow the scattered light from the lumen 00 walls to be collected and imaged within the capsule. Capsule housing 10 also protects lumen 00 from direct contact with the foreign material inside capsule housing 10. Capsule housing 10 is provided a shape that enables it to be swallowed easily and later to pass through of the GI tract. Generally, capsule housing 10 is sterile, made of non-toxic material, and is sufficiently smooth to minimize the chance of lodging within the lumen.

As shown in FIG. 1, capsule system 01 includes illuminating system 12 and a camera that includes optical system 14 and image sensor 16. An image captured by image sensor 16 may be processed by image-based motion detector 18, which determines whether the capsule is moving relative to the portion of the GI tract within the optical view of the camera. Image-based motion detector 18 may be implemented in software that runs on a digital signal processor (DSP) or a central processing unit (CPU), in hardware, or a combination of both software and hardware. Image-based motion detector 18 may have one or more partial frame buffers, a semiconductor nonvolatile archival memory 20 may be provided to allow the images to be retrieved at a docking station outside the body, after the capsule is recovered. System 01 includes battery power supply 24 and an output port 28. Capsule system 01 may be propelled through the GI tract by peristalsis.

Illuminating system 12 may be implemented by LEDs. In FIG. 1, the LEDs are located adjacent the camera's aperture, although other configurations are possible. The light source may also be provided, for example, behind the aperture. Other light sources, such as laser diodes, may also be used. Alternatively, white light sources or a combination of two or more narrow-wavelength-band sources may also be used. White LEDs are available that may include a blue LED or a violet LED, along with phosphorescent materials that are excited by the LED light to emit light at longer wavelengths. The portion of capsule housing 10 that allows light to pass through may be made from bio-compatible glass or polymer.

Optical system 14, which may include multiple refractive, diffractive, or reflective lens elements, provides an image of the lumen walls on image sensor 16. Image sensor 16 may be provided by charged-coupled devices (CCD) or complementary metal-oxide-semiconductor (CMOS) type devices that convert the received light intensities into corresponding electrical signals. Image sensor 16 may have a monochromatic response or include a color filter array such that a color image may be captured (e.g. using the RGB or CYM representations). The analog signals from image sensor 16 are preferably converted into digital form to allow processing in digital form. Such conversion may be accomplished using an analog-to-digital (A/D) converter, which may be provided inside the sensor (as in the current case), or in another portion inside capsule housing 10. The A/D unit may be provided between image sensor 16 and the rest of the system. LEDs in illuminating system 12 are synchronized with the operations of image sensor 16. One function of control module 22 is to control the LEDs during image capture operation.

Motion detection module 18 selects an image to retain when the image shows enough motion relative to the previous image in order to save the limited storage space available. The images are stored in an on-board archival memory system 20. The output port 26 shown in FIG. 1 is not operational in vivo but uploads data to a work station after the capsule is recovered, having passed from the body. Motion detection can also be used to regulate the image capture rate (i.e., the frequency at which the camera captures an image). It is desirable to increase the capture rate when the capsule is in motion. If capsule remains at the same place, it may be desirable to capture an image less frequently to save battery power.

Figure 2:
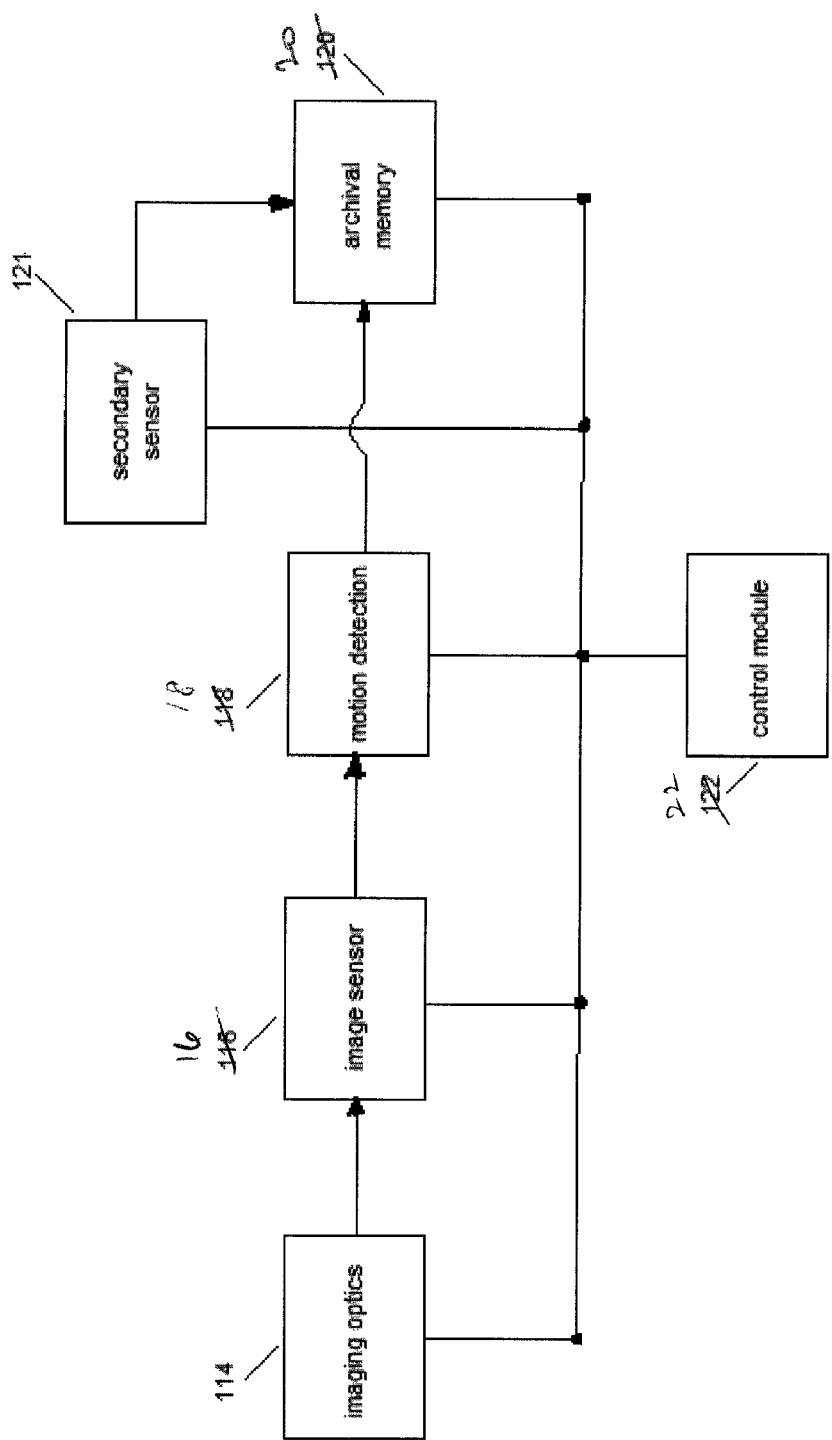
FIG. 2 is a functional block diagram of information flow during capsule camera operation in capsule system 01.

FIG. 2 is a functional block diagram of information flow during capsule camera operation. Except for optical system 114, all of these functions may be implemented on a single integrated circuit. As shown in FIG. 2, optical system 114, which represents both illumination system 12 and optical system 14, provides an image of the lumen wall on image sensor 16. Some images will be captured but not stored in the archival memory 20, based on the motion detection circuit 18, which decides whether or not the current image is sufficiently different from the previous image. An image may be discarded if the image is deemed not sufficiently different from a previous image. Secondary sensors (e.g., pH, thermal, or pressure sensors) may be provided. The data from the secondary sensors are processed by the secondary sensor circuit 121 and provided to archival memory system 20. Measurements made may be provided time stamps. Control module 22, which may consist of a microprocessor, a state machine or random logic circuits, or any combination of these circuits, controls the operations of the modules. For example, control module 22 may use data from image sensor 16 or motion detection circuit 18 to adjust the exposure of image sensor 16.

Archival memory system 20 can be implemented by one or more nonvolatile semiconductor memory devices. There are numerous memory types that can be used; even photographic films can be used for image sensing and storage. Since the image data are digitized for digital image processing techniques, such as motion detection, memory technologies that are compatible with digital data are selected. Of course, semiconductor memories mass-produced using planar technology (which represents virtually all integrated circuits today) are the most convenient. Such memories are low-cost and may be obtained from multiple sources. Semiconductor memories are most compatible because they share common power supply with the sensors and other circuits in capsule system 01, and require little or no data conversion when interfaced with an upload device at output port 26. Archival memory system 20 preserves the data collected during the operation, after the operation while the capsule is in the body, and after the capsule has left the body, up to the time the data is uploaded. This period of time is generally less than a few days. A nonvolatile memory is preferred because data is held without power consumption, even after the capsule's battery power has been exhausted. Suitable non-volatile memory includes flash memories, write-once memories, or program-once-read-once memories. Alternatively, archival memory system 20 may be volatile and static (e.g., a static random access memory (SRAM) or its variants, such as VSRAM, PSRAM). Alternately, the memory could be a dynamic random access memory (DRAM).

Archival memory 20 may be used to hold any initialization information (e.g., boot-up code and initial register values) to begin the operations of capsule system 01. The cost of a second non-volatile or flash memory may therefore be saved. That portion of the non-volatile can also be written over during operation to store the selected captured images.

Figure 3:
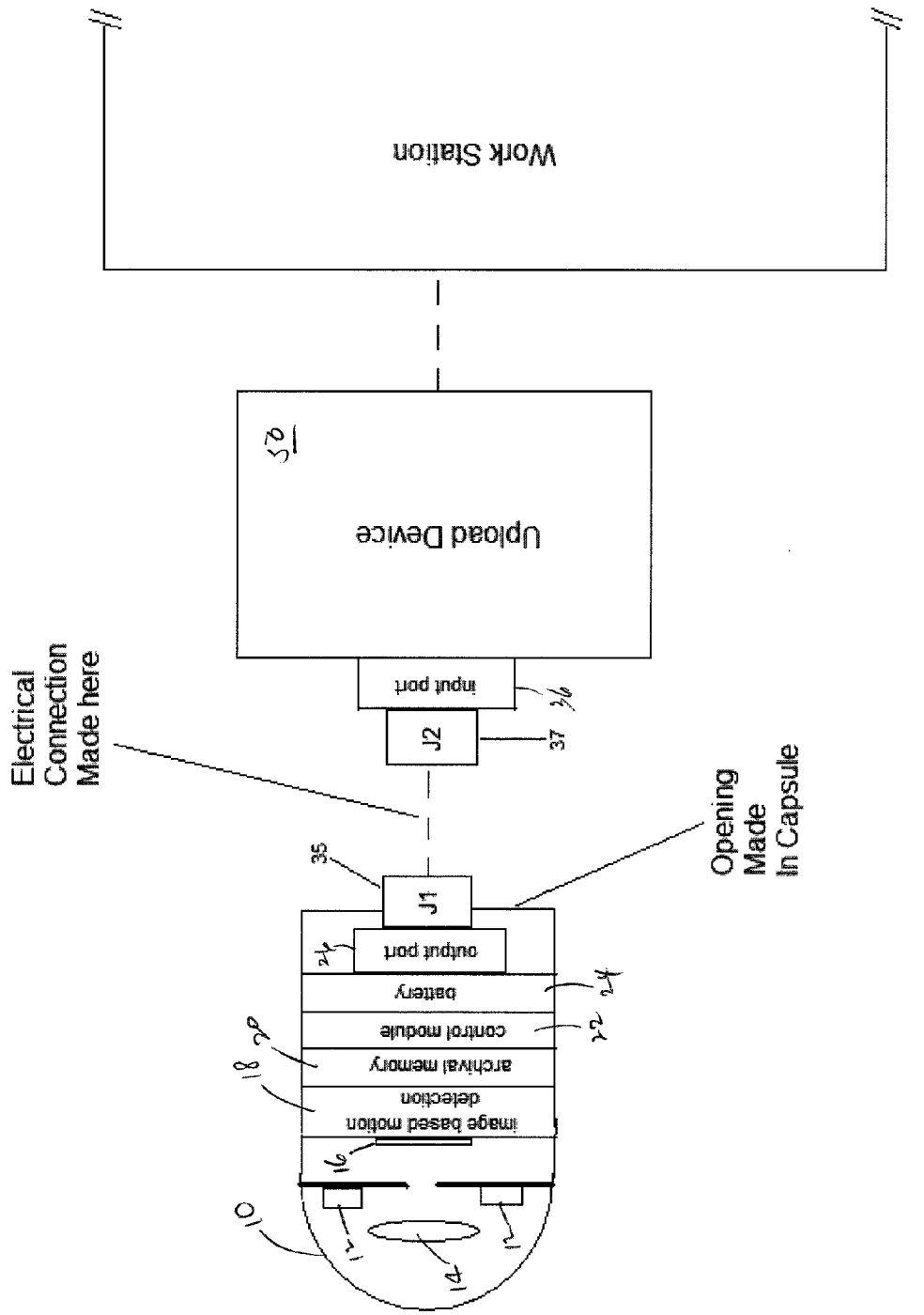
FIG. 3 is a functional block diagram illustrating the data transferring process from capsule system 01 to a workstation.

After the capsule passes from the body, it is retrieved. Capsule housing 10 is opened and input port 16 is connected to an upload device for transferring data to a computer workstation for storage and analysis. The data transferring process is illustrated in the functional block diagram of FIG. 3. As shown in FIG. 3, output port 26 of capsule system 01 includes an electrical connector 35 that mates with connector 37 at an input port of an upload device. Although shown in FIG. 3 to be a single connector, these connectors may be implemented as several conductors to allow data to be transferred serially or over a parallel bus, and so that power may be transferred from the upload device to the capsule, thereby obviating the need for the capsule battery to provide power for the data upload.

To make the electrical connection to output port 26, capsule housing 10 may be breached by breaking, cutting, melting, or another technique. Capsule housing 10 may include two or more parts that are pressure-fitted together, possibly with a gasket, to form a seal, but that can be separated to expose connector 35. The mechanical coupling of the connectors may follow the capsule opening process or may be part of the same process. These processes may be achieved manually, with or without custom tooling, or may be performed by a machine automatically or semi-automatically.

Figure 4:
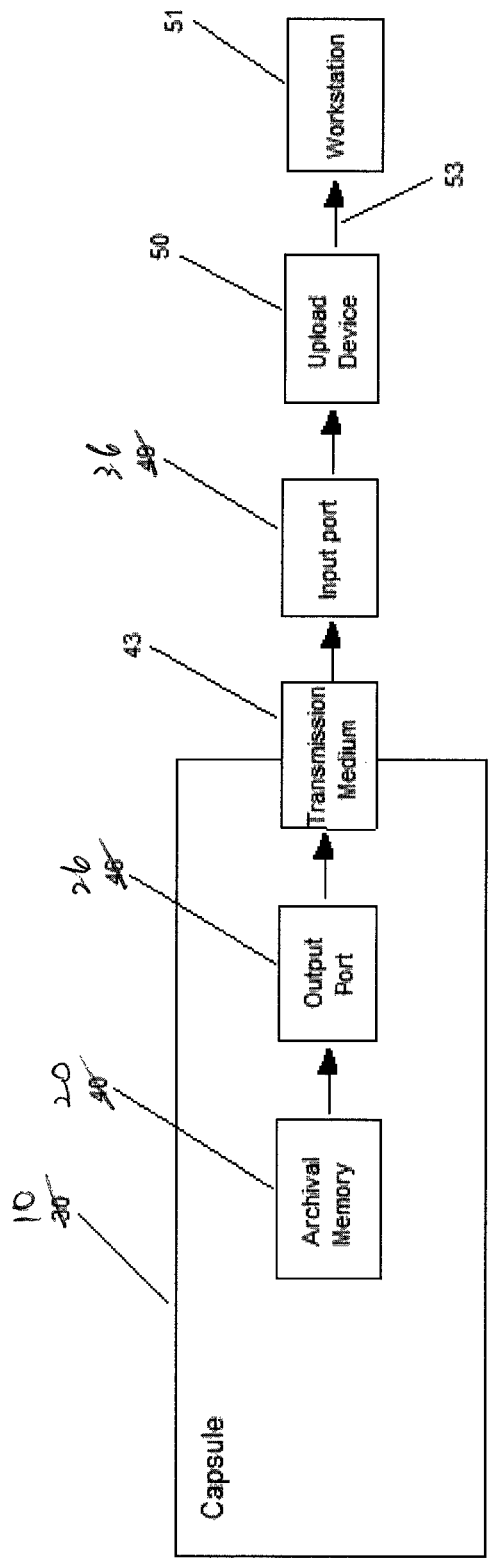
FIG. 4 is a functional block diagram illustrating the data upload process from a capsule, showing information flow from capsule system 01 to workstation 51.

FIG. 4 illustrates the data transfer process, showing information flow from capsule system 01 to workstation 51, where it is written into a storage medium such as a computer hard drive. As shown in FIG. 4, data is retrieved from archival memory 20 over transmission medium 43 between output port 26 of capsule system 01 and input port 36 of upload device 50. The transmission link may use established or custom communication protocols. The transmission medium may include the connectors 35 and 37 shown in FIG. 3 and may also include cabling not shown in FIG. 3. Upload device 50 transfers the data to a computer workstation 51 through interface 53, which may be implemented by a standard interface, such as a USB interface. The transfer may also occur over a local-area network or a wide-area network. Upload device 50 may have memory to buffer the data.

Figure 5:
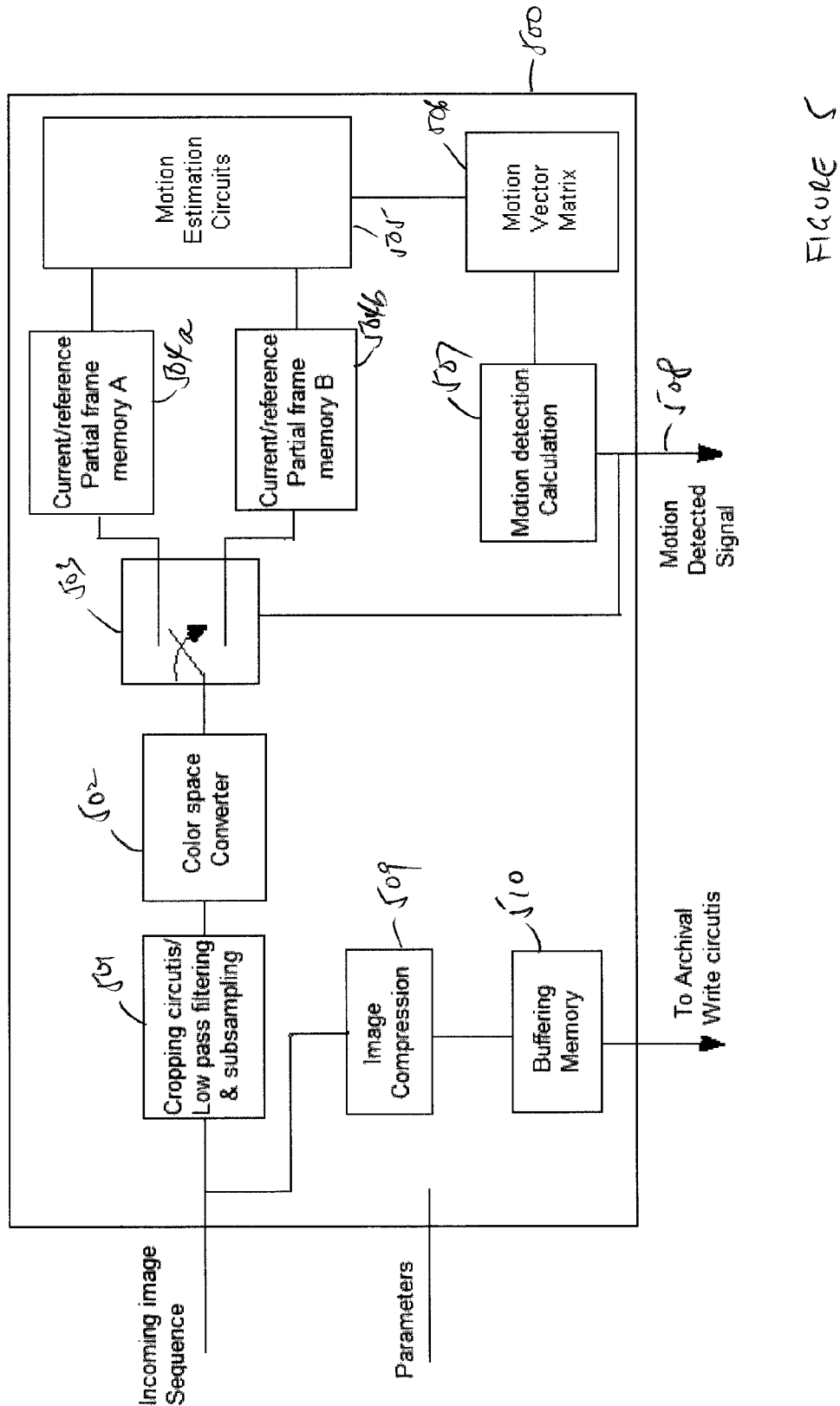
FIG. 5 is a block diagram illustrating implementation 500 for motion detector 18, according to one embodiment of the present invention.
Figure 6:
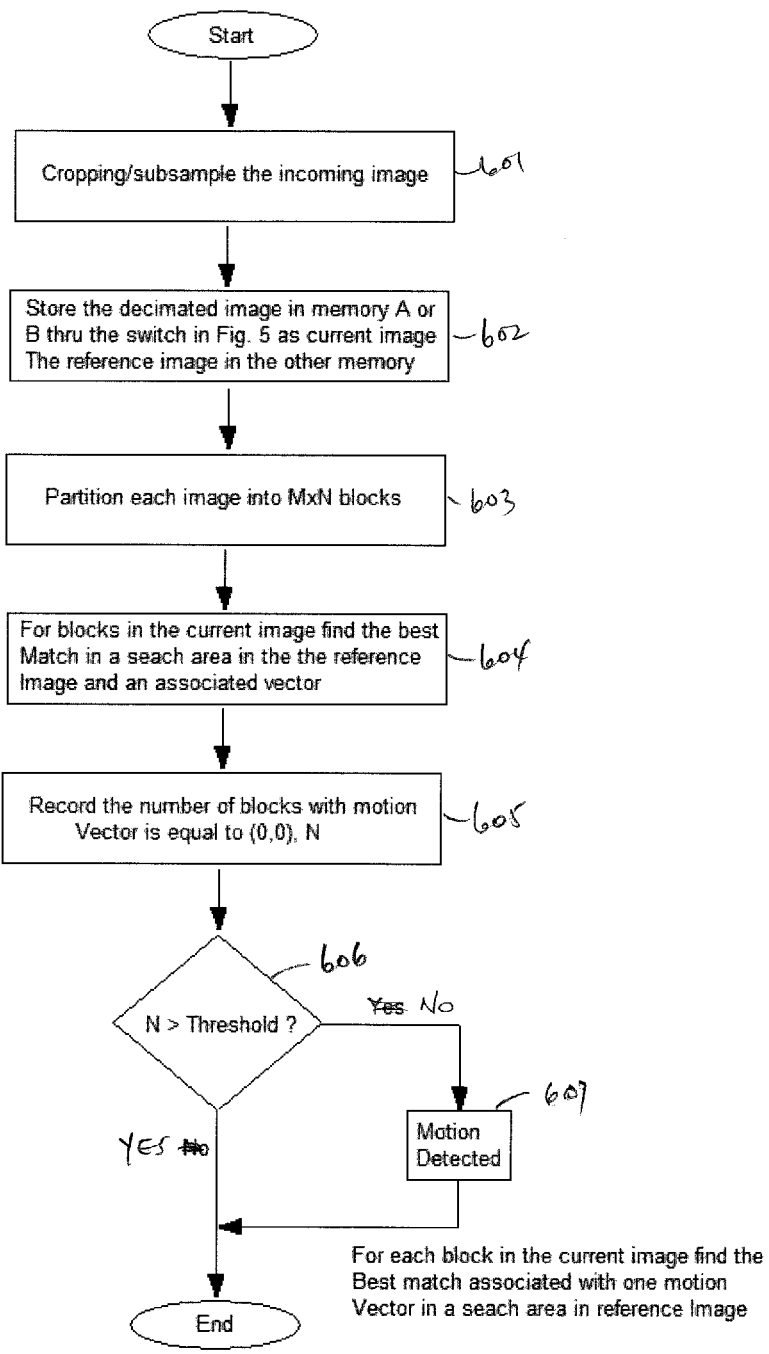
FIG. 6 is a flow chart illustrating the operations related to motion detection in implementation 500 of FIG. 5, according to one embodiment of the present invention.
Figure 7:
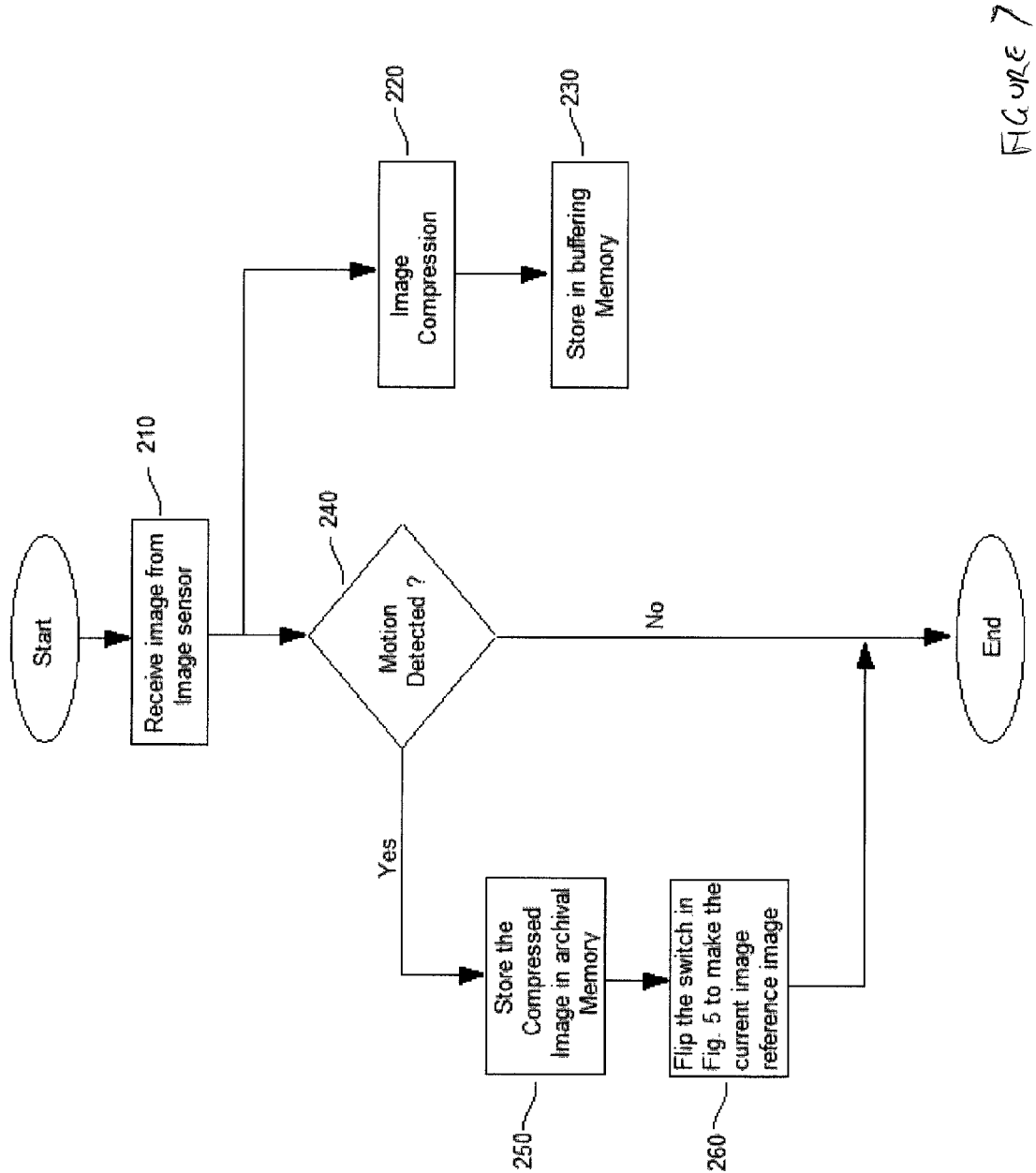
FIG. 7 is a flow chart illustrating the operations relating to data storage in implementation 500 of FIG. 5, according to one embodiment of the present invention.

FIGS. 5-7 are, respectively, (a) a block diagram illustrating an implementation (labeled 500 in FIG. 5) for motion detector 18, (b) a flow chart illustrating the operations related to motion detection in implementation 500, and (c) a flow chart illustrating the operations relating to data storage in implementation 500, according to one embodiment of the present invention. As shown in FIGS. 5-7, the current digitized image is received (step 210, FIG. 7) and processed in processing circuit 501, using such techniques as cropping, low-pass filtering, sub-sampling and decimation to prepare the image data for further processing at a selected resolution (step 601, FIG. 6). One portion of the processed image is selected for motion detection. This portion may be represented at a higher resolution than the rest of the image.

A color space conversion may be performed in color space converter 502, which converts the image data from, for example, an RGB representation to a CYM representation, or a YUV representation (i.e., lumas and chromas). In this manner, the image may be captured or archived using a different representation than that used for motion detection. The image is then stored in one of two partial frame buffer 504a and 504b (step 602, FIG. 6). The other one of partial frame buffers 504a and 504b contains a reference image, which is the previous stored image.

Circuit 505 compares the current image with the reference image by evaluating motion vectors identified in motion estimation circuit 505. To identify the motion vectors, at step 603 (FIG. 6), the current image and the reference image are each partitioned into M*N blocks, where M and N are integers. For each block in the current image, a best match is found in the reference image in a search area within a selected distance of the block's position (step 604, FIG. 6). The motion vector for the block is the translation vector between the block and its best match. The motion vectors are stored in motion vector matrix 506. Motion detection calculation or evaluation circuit 507 then evaluates the results to determine whether or not the current image is to be stored. In this instance, the number of zero motion vectors (i.e., [0, 0]) is counted. If the total number of zero motion vectors exceed a threshold (step 606 or 240, FIG. 6 or 7), no motion is detected. Conversely, if the number of zero vectors is less than the threshold, motion is detected. The threshold may be hardwired into the circuit design, obtained from a non-volatile memory (e.g., flash memory) during the initialization process or received from outside using wireless transmission (see below). During operation, the threshold value may be read from a register, either in control module 22 or in motion detector 18. Alternatively, the threshold may also be dynamically determined based on how much free space remains in archival memory system 20 or buffering memory 510.

Note that, in some embodiments, only motion vectors in the forward direction along the length of the GI tract (i.e., +y direction) are of interest. Movement in the −y direction represents a retrograde motion. Presumably, the optical view after the retrograde motion has already been captured previously. Alternatively, we can reduce the weight given to the x-component of the motion vector, so that some motion vectors with some x-component motion can be rounded to [0, 0].

If motion is detected, a motion detection signal 508 is asserted to cause a compressed copy of the current image (stored in buffering memory 510) to be stored in archiving memory 20 (step 250, FIG. 7). The partial frame buffer 504a or 504b that contains the current image is marked to become the new reference image, while the other partial frame buffer (i.e., the buffer containing the current reference image) is made available to be overwritten by the next current image (step 260, FIG. 7). If the current image is not to be stored, the partial frame buffer containing the current image can be overwritten by the next current image. Before the current image is stored in archival memory 20, image compression circuit 509 compresses the current image according to a selected data compression algorithm (step 220, FIG. 7). The compressed image in data buffer 510 is then transferred into archival memory 20 under control by control module 22 (step 230, FIG. 7). Of course, steps 220 and 230 can be performed concurrently with motion detection.

Figure 8:
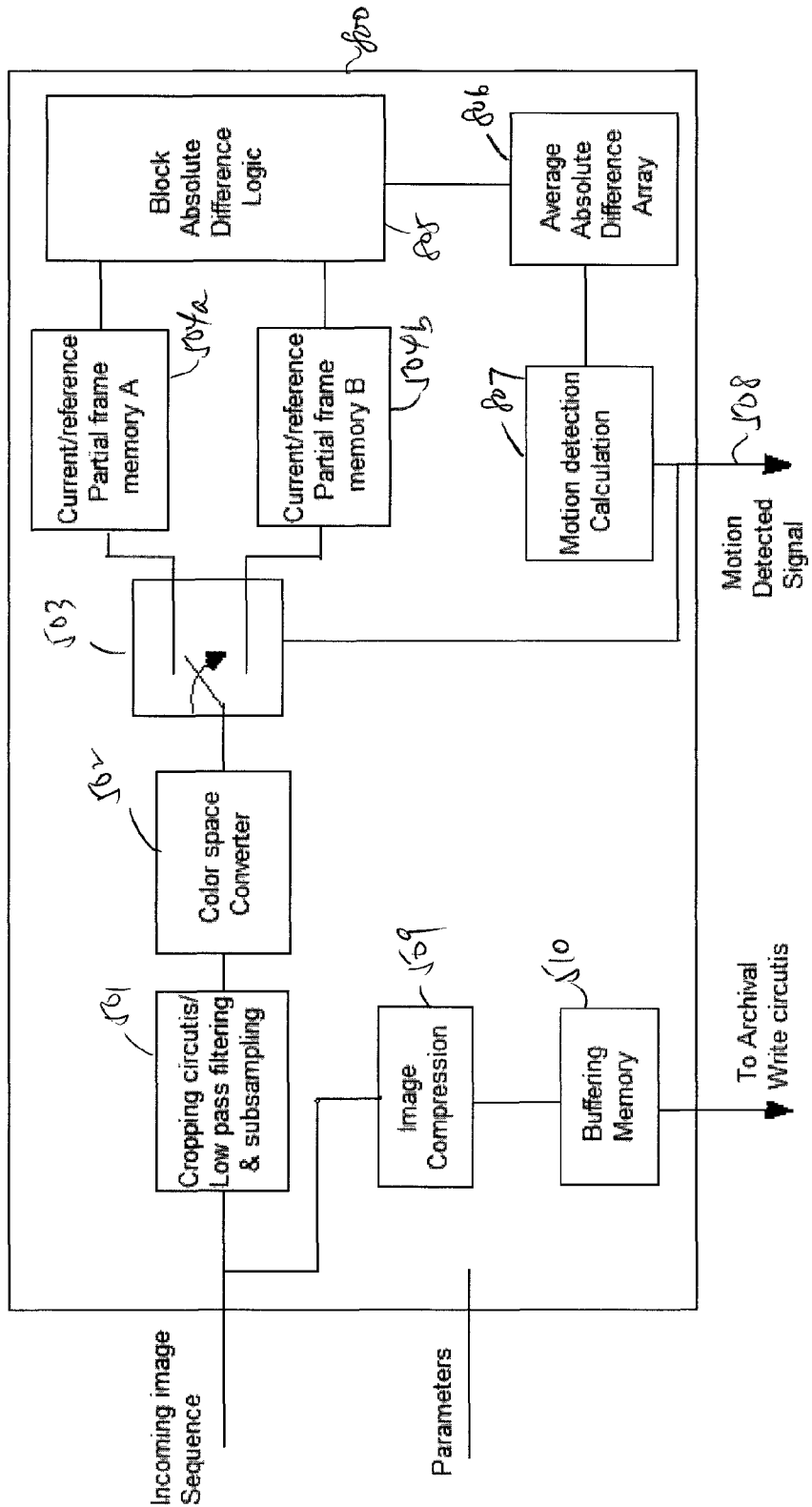
FIG. 8 is a block diagram illustrating implementation 800 for motion detector 18, according to one embodiment of the present invention.
Figure 9:
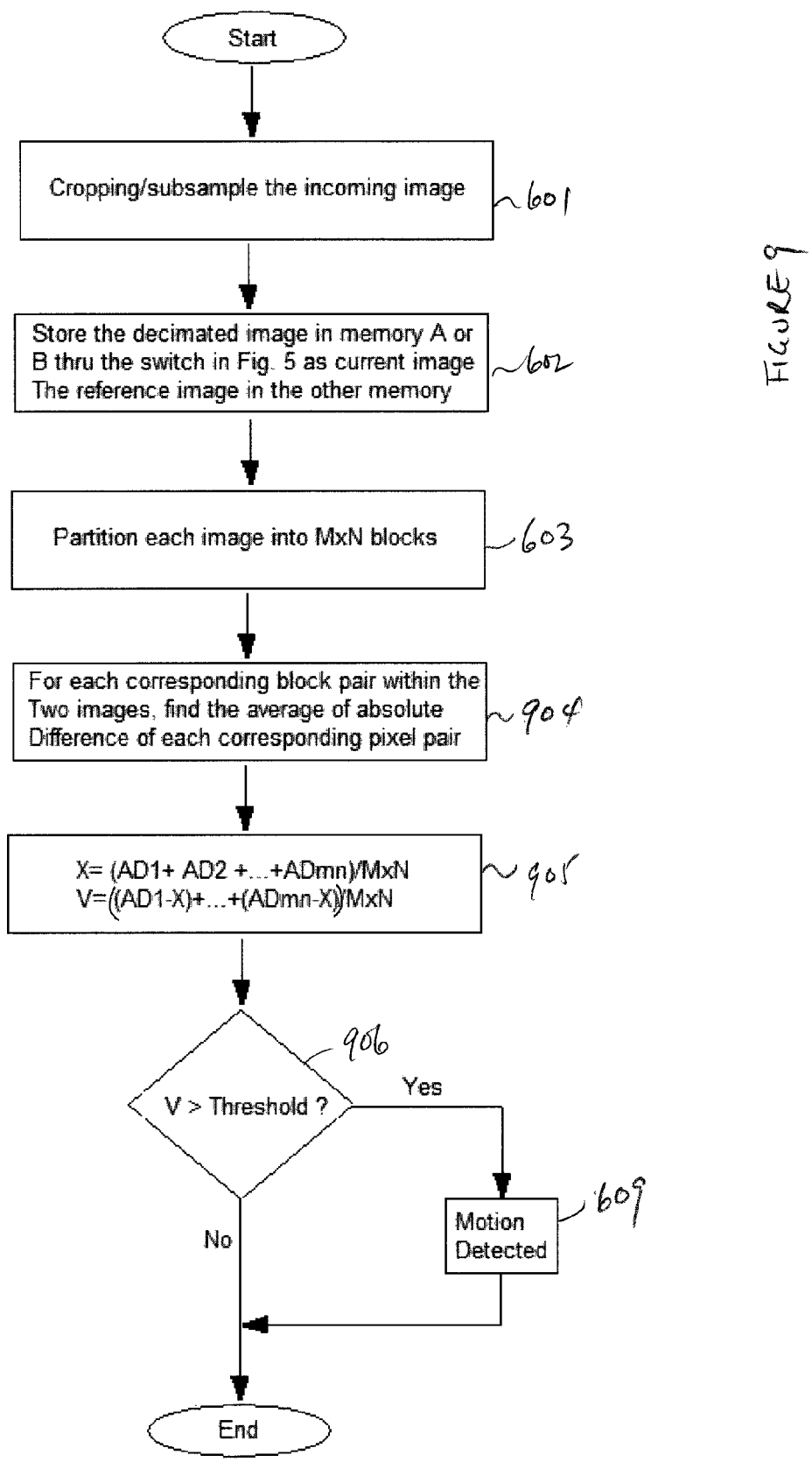
FIG. 9 is a flow chart illustrating the operations related to motion detection in implementation 800 of FIG. 8, according to one embodiment of the present invention.

Instead of using motion vectors, motion detection can also be performed using an absolute difference between the current image and the reference image. FIG. 8 shows an implementation 800 using the absolute difference approach. Implementation 800 operates substantially the same way as implementation 500 of FIG. 5, except that motion estimation circuits 505, motion vector matrix 506 and motion detection calculation circuit 508 of FIG. 5 are replaced by block absolute difference logic 805, average absolute difference array 806 and motion detection circuit 807. FIG. 9 is a flow chart illustrating the operations related to motion detection in implementation 800. FIG. 9 shares a number of operations with FIG. 6 discussed above. To simplify the following discussion, operations in FIG. 9 that are substantially the same as corresponding steps in FIG. 6 are assigned the same reference numeral. The storage operations for implementation 800 are substantially the same as the corresponding operations in implementation 500. Those operations are referenced to FIG. 7.

As shown in FIGS. 7-9, the current digitized image is received (step 210, FIG. 7) and processed in processing circuit 501, using such techniques as cropping, low-pass filtering, sub-sampling and decimation to prepare the image data for further processing at a selected resolution (step 601, FIG. 9). One portion of the processed image is selected for motion detection. As mentioned above, this portion may be represented at a higher resolution than the rest of the image. As in implementation 500, a color space conversion may be performed in color space converter 502. The image is then stored in one of two partial frame buffer 504a and 504b (step 602, FIG. 9). The other one of partial frame buffers 504a and 504b contains a reference image, which is a previous stored image.

Circuit 805 compares the current image with the reference image by evaluating absolute differences between the two images. To identify the differences, at step 603 (FIG. 9), the current image and the reference image are each partitioned into M*N blocks, where M and N are integers. In each corresponding block pair (i.e., a block in the current image and the block in the corresponding position in the reference image), an absolute difference between each pixel (e.g., in luminance) in the current image and the corresponding pixel in the reference image is found in block absolute difference logic circuit 805 (step 904, FIG. 9). An average for the absolute difference, denoted by $AD_i$, $i=1, \ldots, M*N$, for the block is found and provided in average absolute difference array 806. Motion detection calculation circuit 507 then evaluates the results to determine if the current image is to be stored. In this instance, at step 905 (FIG. 9), a mean absolute difference $$\bar{x} = \frac{1}{M*N} \sum_i AD_i$$

over the portion of image is calculated. Then, the total variance, given by $$v = \frac{1}{M*N} \sum_i |AD_i - \bar{x}|,$$

is then found. If the total variance exceeds a threshold (step 906 or 240, FIG. 9 or 7), motion is deemed detected. Conversely, if the total variance v is less than the threshold, no motion is deemed detected. If motion is detected, a motion detection signal 508 is asserted to cause the current image to be stored in archiving memory 20 (step 250, FIG. 7). The partial frame buffer 504a or 504b that contains the current image is marked to become the new reference image, while the other partial frame buffer (i.e., the partial frame buffer containing the current reference image) is made available to be overwritten by the next current image (step 260, FIG. 7). If the current image is not to be stored, the partial frame buffer containing the current image can be overwritten by the next current image. Before the current image is stored in archival memory 20, image compression circuit 509 compresses the current image according to a selected data compression algorithm (step 220, FIG. 7). The compressed image in data buffer 510 is then transferred into archival memory 20 under control by control module 22 (step 230, FIG. 7). Of course, steps 220 and 230 can be performed concurrently with motion detection.

Figure 10:
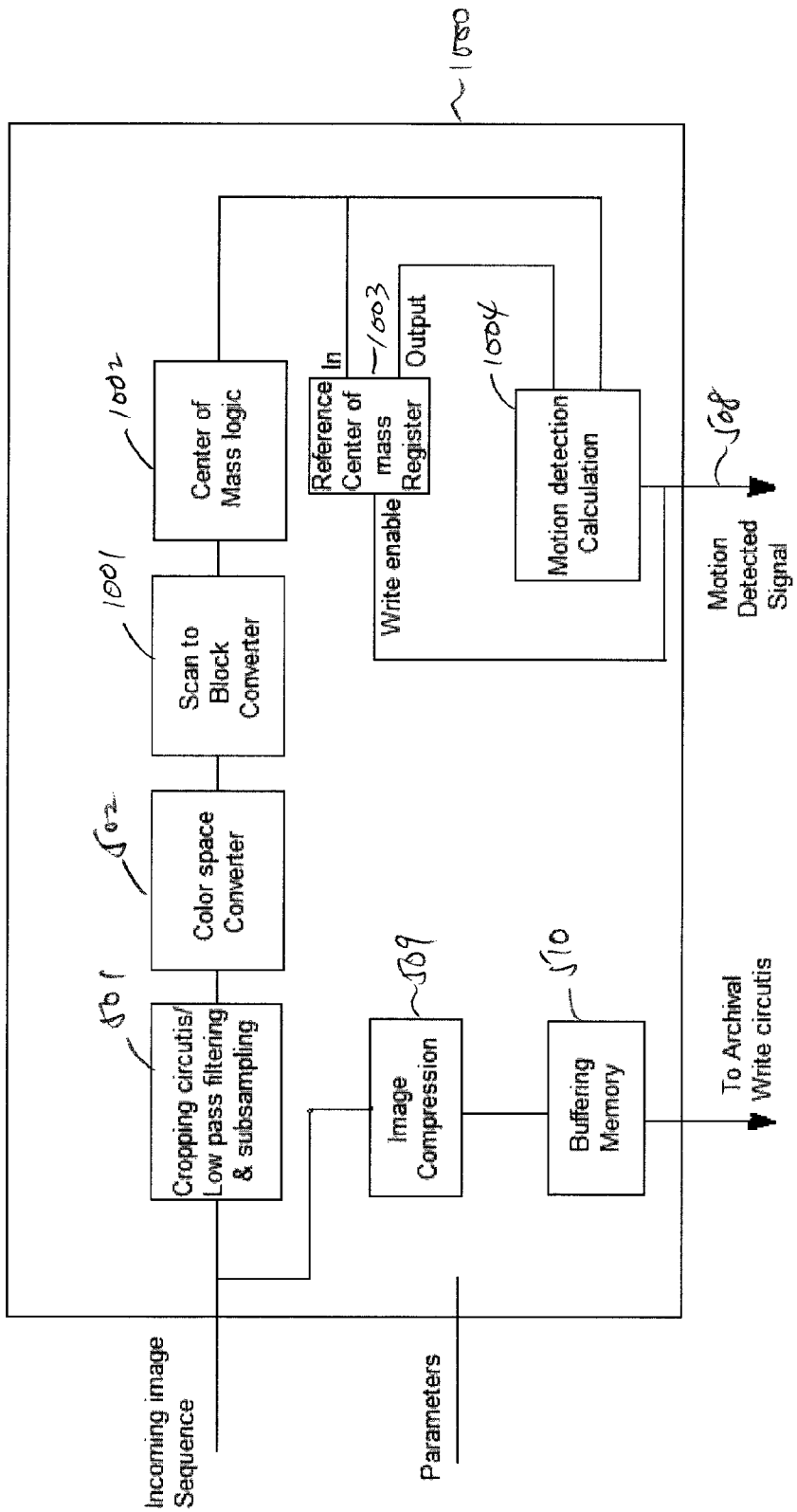
FIG. 10 is a block diagram illustrating implementation 1000 for motion detector 18, according to one embodiment of the present invention.
Figure 11:
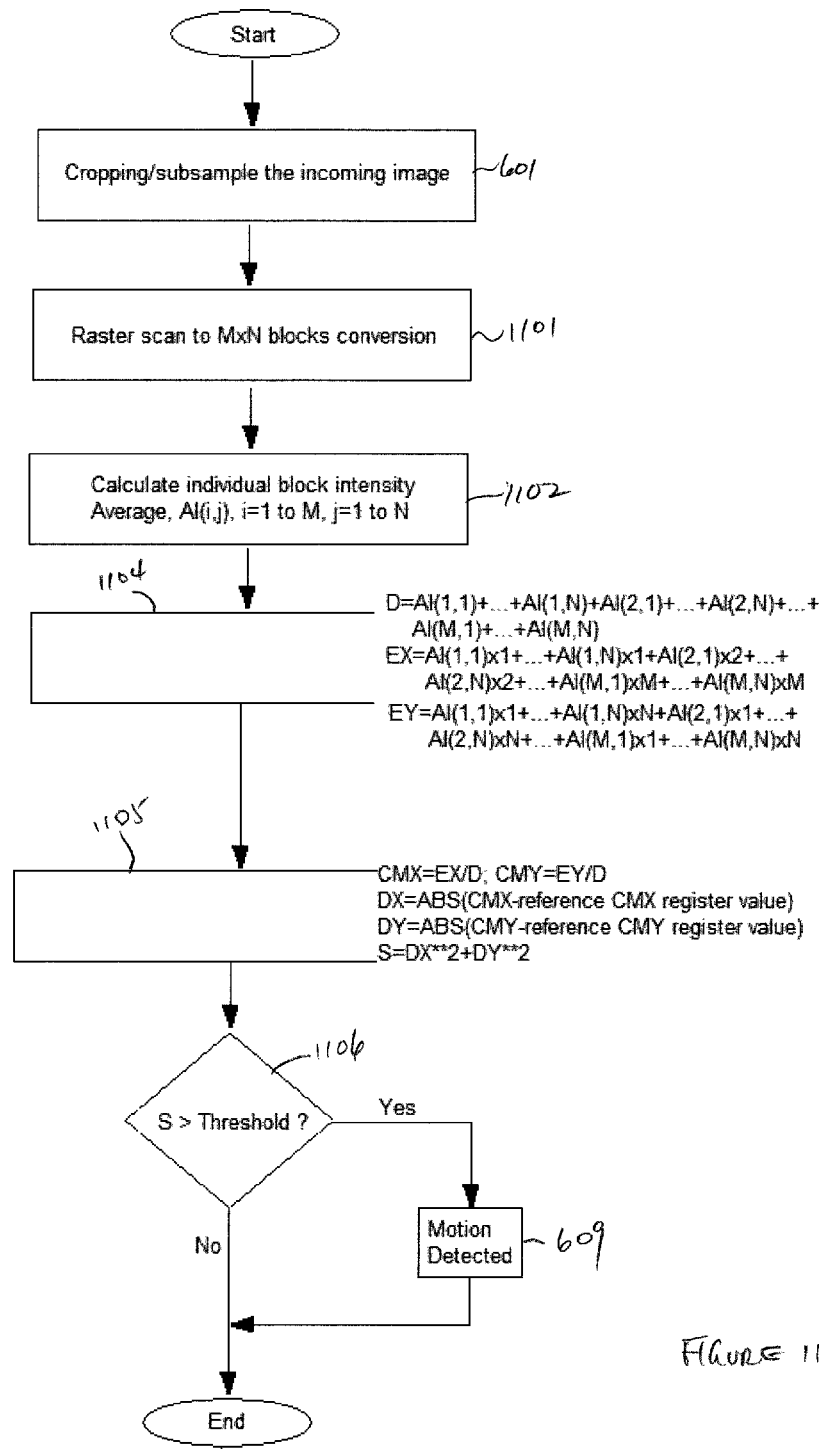
FIG. 11 is a flow chart illustrating the operations related to motion detection in implementation 1000 of FIG. 10, according to one embodiment of the present invention.
Figure 12:
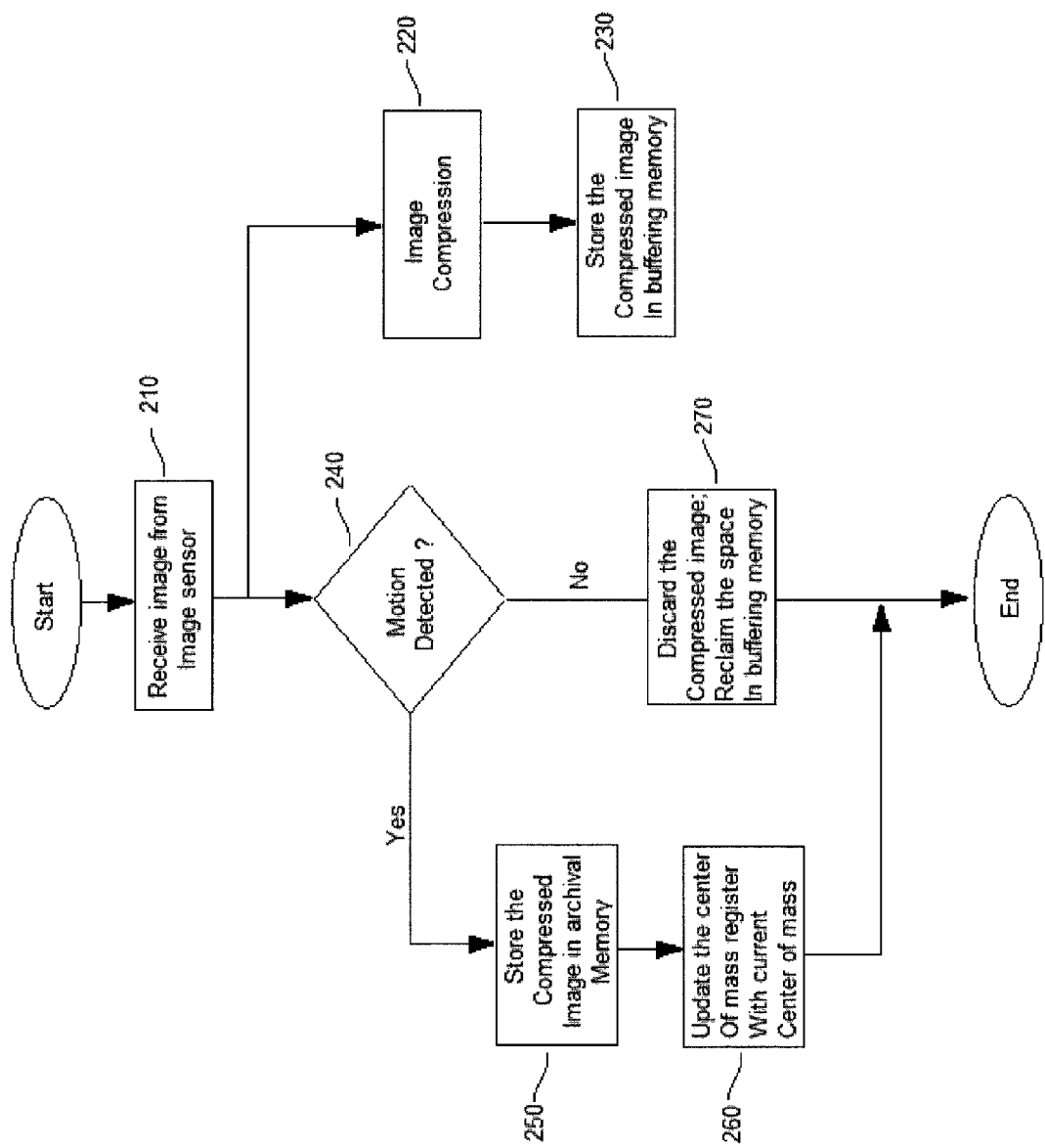
FIG. 12 is a flow chart illustrating the operations related to data storage in implementation 1000 of FIG. 10, according to one embodiment of the present invention.

Instead of using motion vectors or absolute difference, motion detection can also be performed according to yet another embodiment of the present invention, using a "center-of-mass" approach. FIG. 10 shows an implementation 1000 using the center-of-mass approach. Implementation 1000 includes operations that are substantially the same way as corresponding operations in implementation 500 of FIG. 5. These corresponding operations between FIGS. 5 and 10 are assigned the same reference numerals. FIGS. 11-12 are, respectively, flow charts illustrating the operations related to motion detection and data storage in implementation 1000. FIGS. 11-12 share a number of operations with FIGS. 6-7 discussed above. To simplify the following discussion, operations in FIGS. 11-12 that are substantially the same as corresponding operations in FIGS. 6-7 are assigned the same reference numeral.

As shown in FIGS. 10-12, the current digitized image is received (step 210, FIG. 12) and processed in processing circuit 501, using such techniques as cropping, low-pass filtering, sub-sampling and decimation to prepare the image data for further processing at a selected resolution (step 601, FIG. 11). As in implementation 500, a color space conversion may be performed in color space converter 502. In implementation, the luminance value in each pixel of the current image is stored in M*N blocks in raster scan-to-block converter 1001 (step 1101, FIG. 11). Center-of-mass logic circuit 1002 then calculates the center-of-mass for the image. To calculate the center-of-mass, the average intensity $AI_{ij}$, $i=1, \ldots, M$ and $j=1, \ldots, N$, of each block is first calculated (step 1104, FIG. 11). A total D of the average intensities over all the blocks, i.e., $$D = \sum_{i,j} AI_{ij}$$

is calculated. Then the moments $E_x$ and $E_y$ along the orthogonal directions are calculated. The moments are given by:

$$E_x = \sum_{i,j} i^* AI_{ij} \text{ and } E_x = \sum_{i,j} j^* AI_{ij}.$$

The center-of-mass $CM(CM_x, CM_y)$ for the image is then provided by:

$$CM_x = \frac{E_x}{D}$$

and $$CM_y = \frac{E_y}{D}.$$

The reference center-of-mass $CM_{ref}(CM_{ref\_x}, CM_{ref\_y})$ value, corresponding to the center-of-mass of the previous stored image, is stored in reference register 1003. Motion detection calculation circuit 1004 then evaluates the results to determine whether or not the current image is to be stored. In this instance, at step 1105 (FIG. 11), the values $D_x$ and $D_y$ of the differences between the center-of-mass of the current image and the center-of-mass of the reference image along the orthogonal directions are then calculated. These differences are given by:

$D_x = CM_x - CM_{ref\_x}$ and $D_y = CM_y - CM_{ref\_y}$. The metric $S = D_x^2 + D_y^2$ then provides a measure for the motion in the current image. If metric S exceeds a threshold (step 1106 or 240, FIG. 11 or 12), motion is deemed detected. Conversely, if the metric S is less than the threshold, no motion is deemed detected. In some embodiments, only motion in the forward direction along the GI tract (i.e., +y direction) is of interest. Movement in the −y direction represents a retrograde motion. In that situation, the metric S may simply be $D_y$ or $D_y^2$. Alternatively, a greater weight may be given to a shift in center-of-mass in the y direction: $S = D_x^2 + wD_y^2$, $w > 1$.

If motion is detected, a motion detection signal 508 is asserted to cause a compressed copy of the current image (in buffering memory 510) to be stored in archiving memory 20 (step 250, FIG. 12). The current center-of-mass value is stored into reference register 1003 (step 260, FIG. 12). Before the current image is stored in archival memory 20, image compression circuit 509 compresses the current image according to a selected data compression algorithm (step 220, FIG. 12). The compressed image in data buffer 510 is then transferred into archival memory 20 under control by control module 22 (step 230, FIG. 12). Of course, steps 220 and 230 can be performed concurrently with motion detection.

In one implementation, the capsule passes naturally from the rectum, is collected by the patient, and is then taken to a clinic where the data is uploaded onto a workstation. Alternatively, the patient can be provided an upload device at her home. When the capsule is retrieved, it may be opened by the patient and a connection is made using the connectors at the input port (upload device side) and output port (capsule side) discussed above. The data is uploaded and then transferred (e.g., transmitted over a telephone line, or a wide area network such as the Internet) to a clinician workstation. Alternatively, the capsule could be removed from the body through another bodily orifice (not the anus), through a catheter, or by surgery.

Alternatively, data may be retrieved from the capsule optically or electromagnetically without breaking the capsule housing. For example, the output port may include a modulated light source, such as an LED, and the input port may include a photodiode sensor. Inductive or capacitive coupling or an radio frequency (RF) link may be other alternatives for data transfer. In these cases, the capsule has to provide power to the output port, or that power is supplied inductively from the upload device. Such solutions may affect the size and cost of the capsule.

The connector at the output port of the capsule may be provided a hermetic or near-hermetic bulkhead feedthrough imbedded in the housing wall, such that an electrical connection can be made between the connector at the output port of the capsule and its mate at the upload device, without breaking the seal. Such an arrangement allows the capsule to be re-used. A capsule that is disposed after a single use is preferable when the cost of sterilizing, recharging, testing, and delivering it repackaged to another patient exceeds or approaches the cost of the capsule. A single-use capsule can be made more compact and cheaper since the memory used need not be re-writable, and the required durability is less than that required of a reusable system.

A desirable alternative to storing the images on-board is to transmit the images over a wireless link. In one embodiment of the present invention, data is sent out through wireless digital transmission to a base station with a recorder. Because available memory space is a lesser concern in such an implementation, a higher image resolution may be used to achieve higher image quality. Further, using a protocol encoding scheme, for example, data may be transmitted to the base station in a more robust and noise-resilient manner. One disadvantage of the higher resolution is the higher power and bandwidth requirements. One embodiment of the present invention transmits only selected images using substantially the selection criteria discussed above for selecting images to store. In this manner, a lower data rate is achieved, so that the resulting digital wireless transmission falls within the narrow bandwidth limit of the regulatory approved Medical Implant Service Communication (MISC) Band. In addition, the lower data rate allows a higher per-bit transmission power, resulting in a more error-resilient transmission. Consequently, it is feasible to transmit a greater distance (e.g. 6 feet) outside the body, so that the antenna for picking up the transmission is not required to be in an inconvenient vest, or to be attached to the body. Provided the signal complies with the MISC requirements, such transmission may be in open air without violating FCC or other regulations.

Figure 13:
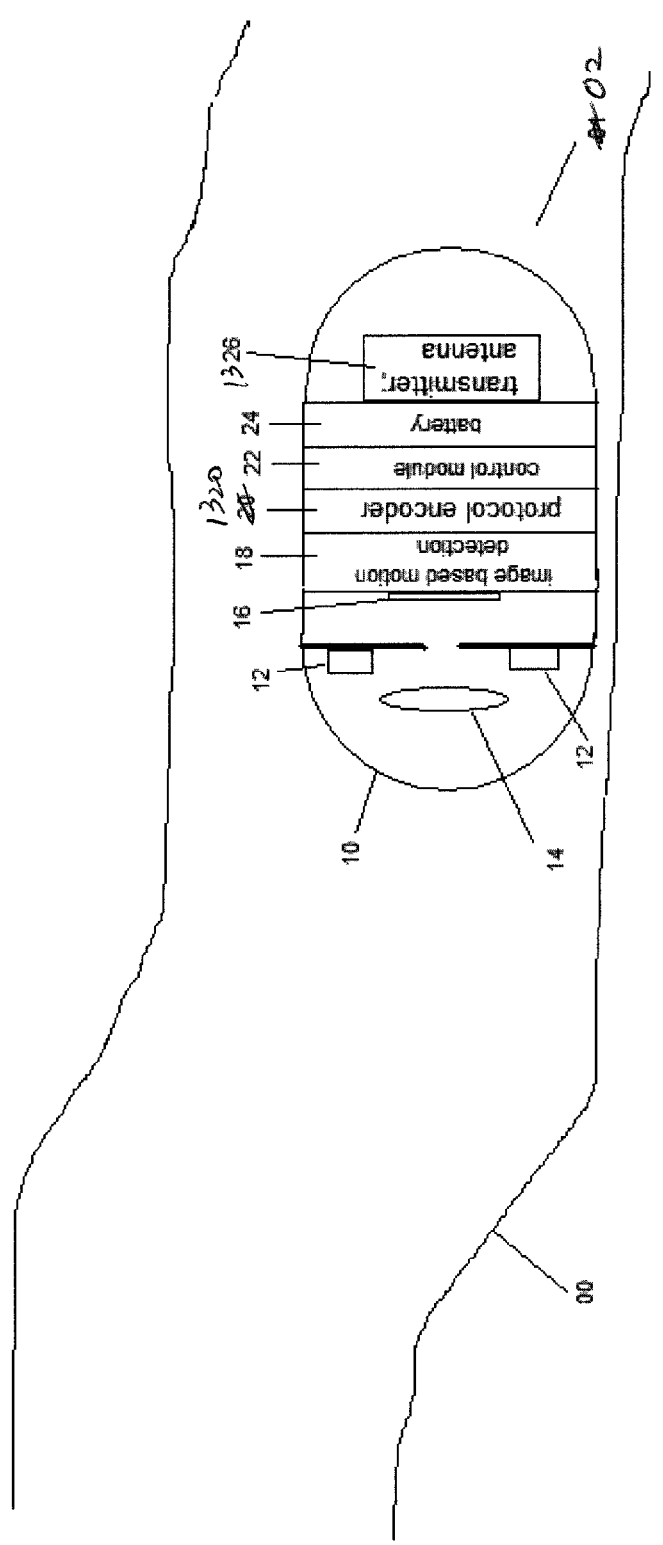
FIG. 13 shows schematically capsule system 02 in the GI tract, according to one embodiment of the present invention, showing the capsule in a body cavity.

FIG. 13 shows swallowable capsule system 02, in accordance with one embodiment of the present invention. Capsule system 02 may be constructed substantially the same as capsule system 01 of FIG. 1, except that archival memory system 20 and output port 26 are no longer required. Capsule system 02 also includes communication protocol encoder 1320 and transmitter 1326 that are used in the wireless transmission. The elements of capsule 01 and capsule 02 that are substantially the same are therefore provided the same reference numerals. Their constructions and functions are therefore not described here again. Communication protocol encoder 1320 may be implemented in software that runs on a DSP or a CPU, in hardware, or a combination of software and hardware, Transmitter 1326 includes an antenna system for transmitting the captured digital image.

Figure 14:
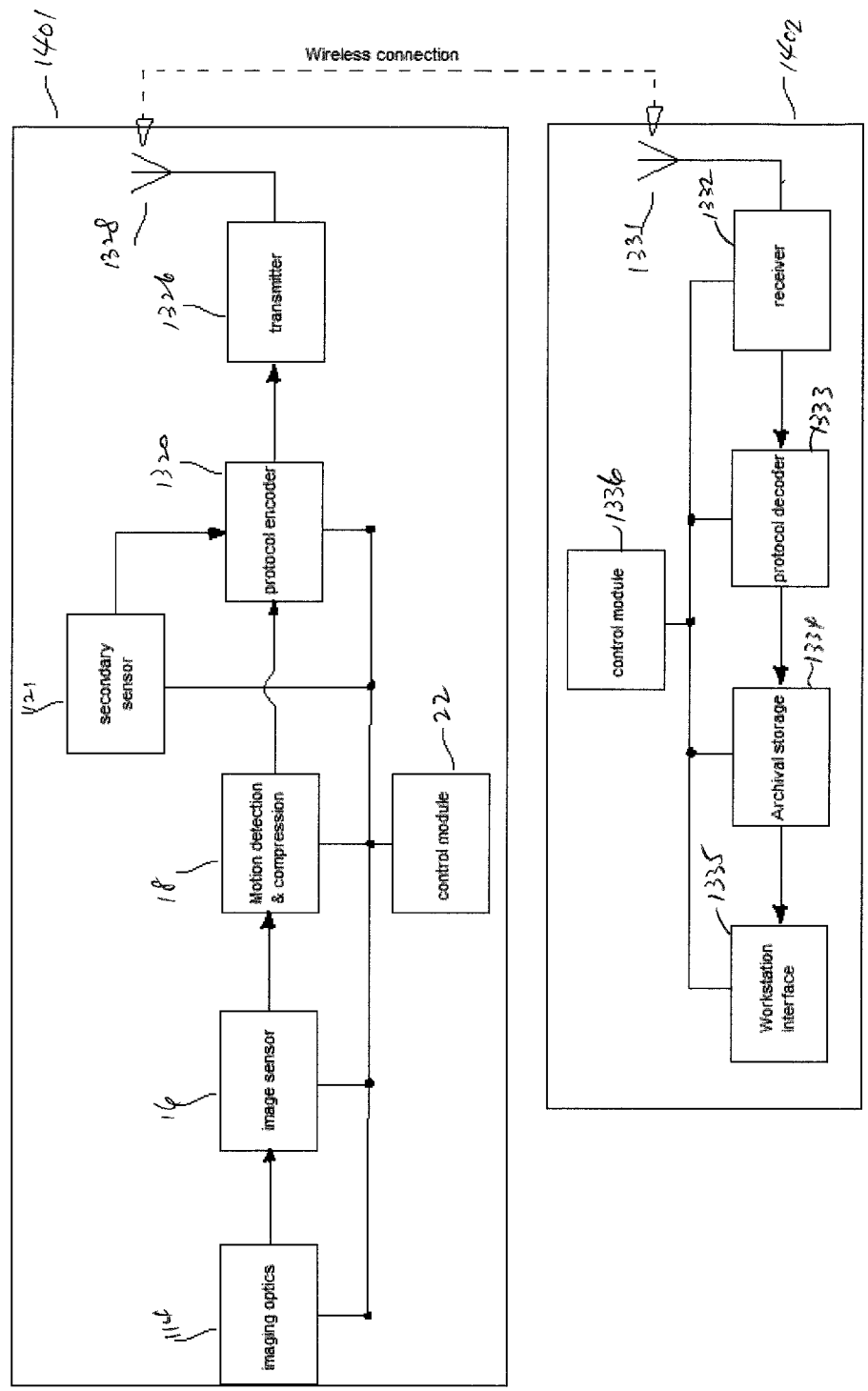
FIG. 14 is a functional block diagram of information flow in implementation 1400 during capsule camera operation in capsule system 02.

FIG. 14 is a functional block diagram of information flow of implementation 1400 of capsule system 02, during capsule camera operation. Functions shown in blocks 1401 and 1402 are respectively the functions performed in the capsule and at an external base station with a receiver 1332. With the exception of optical system 114, the functions in block 1401 may be implemented on a single integrated circuit. As shown in FIG. 14, optical system 114, which represents both illumination system 12 and optical system 14, provides an image of the lumen wall on image sensor 16. Some images will be captured but not transmitted from capsule system 02, based on the motion detection circuit 18, which decides whether or not the current image is sufficiently different from the previous image. All the modules and methods for motion detection discussed above in conjunction with FIGS. 6-12 are also applicable in capsule system 02. An image may be discarded if the image is deemed not sufficiently different from the previous image. An image selected for transmission is processed by protocol encoder 1320 for transmission. Secondary sensors (e.g., pH, thermal, or pressure sensors) may be provided. The data from the secondary sensors are processed by the secondary sensor circuit 121 and provided to protocol encoder 1320. Measurements made may be provided time stamps. Images and measurements processed by protocol encoder 1320 are transmitted through antenna 1328. Control module 22, which may consist of a microprocessor, a state machine or random logic circuits, or any combination of these circuits, controls the operations of the modules in capsule system 02. As mentioned above, the benefits of selecting captured images based on whether the capsule has moved over a meaningful distance or orientation is also applicable to select captured images for wireless transmission. In this manner, an image that does not provide additional information than the previously transmitted one is not transmitted. Precious battery power that would otherwise be required to transmit the image is therefore saved.

As shown in FIG. 14, a base station represented by block 1402 outside the body receives the wireless transmission using antenna 1331 of receiver 1332. Protocol decoder 1333 decodes the transmitted data to recover the captured images. The recovered captured images may be stored in archival storage 1334 and provided later to a workstation where a practitioner (e.g., a physician or a trained technician) can analyze the images. Control module 1336, which may be implemented the same way as control module 22, controls the functions of the base station. Capsule system 02 may use compression to save transmission power. If compression is used in the transmitted images in motion detector 18, a decompression engine may be provided in base station 1402, or the images may be decompressed in the workstation when they are viewed or processed. A color space converter may be provided in the base station, so that the transmitted images may be represented in a different space used in motion detection than the color space used for image data storage.

Figure 15:
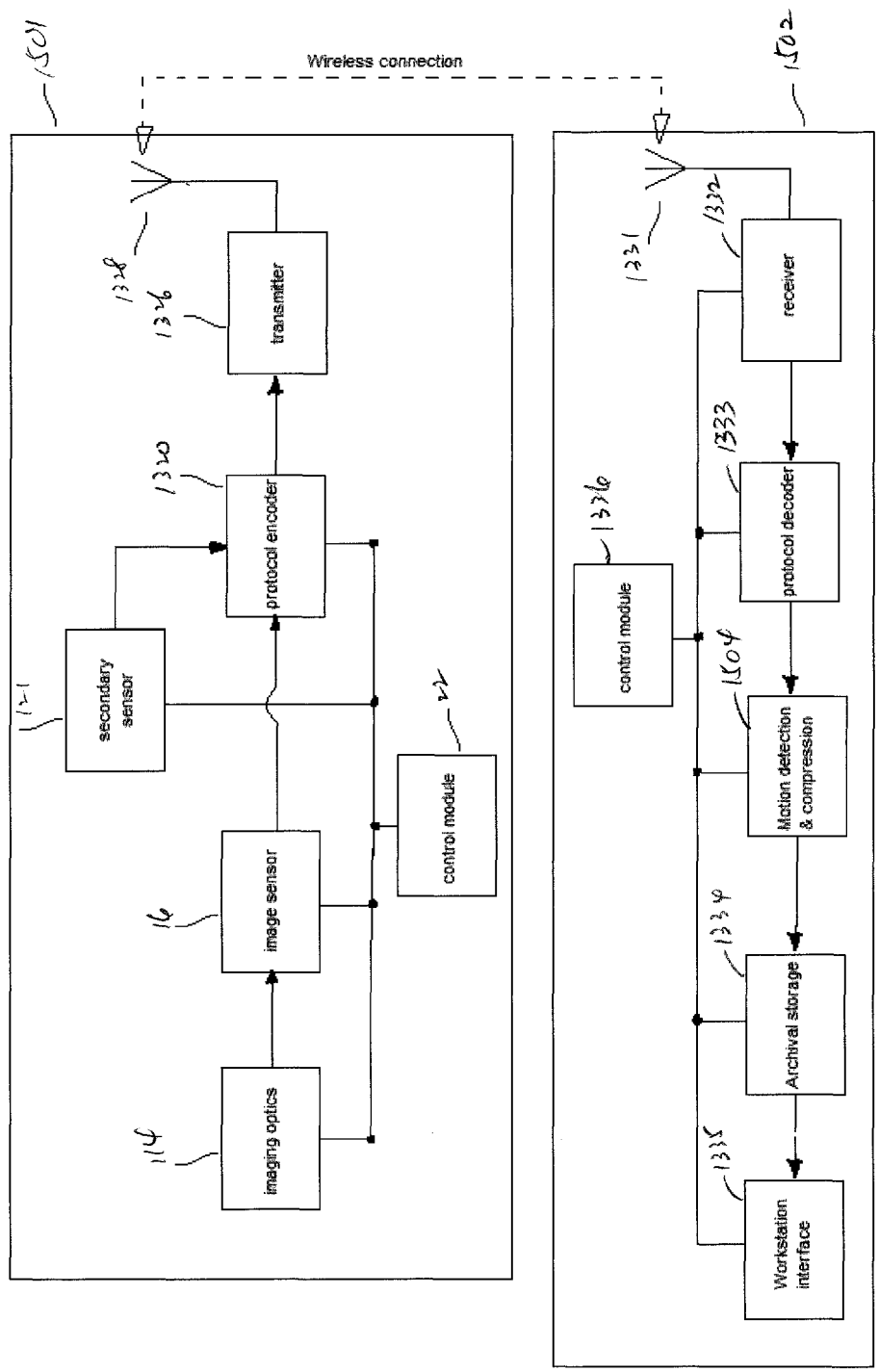
FIG. 15 is a functional block diagram of information flow in implementation 1500 during capsule camera operation in capsule system 02.

Alternatively, as motion detection and image compression are functions that require sophisticated software or circuits, or both. If a simpler implementation is desired, motion detection may be performed in the base station to screen out redundant images. As the number of images that may be captured along the entire length of GI tract is large, motion detection at the base station performs this screening function. In addition, image compression further reduces the required storage space necessary in archival memory 1334. Implementation 1500, in which motion detection and compression are performed in motion detection and compression module 1504 in base station 1502 is shown in FIG. 15. The modules in the capsule portion 1501 of FIG. 15 are substantially the same as the modules in the capsule portion 1401 of FIG. 14, except that motion detection and compression module 18 is not implemented.

Figure 16:
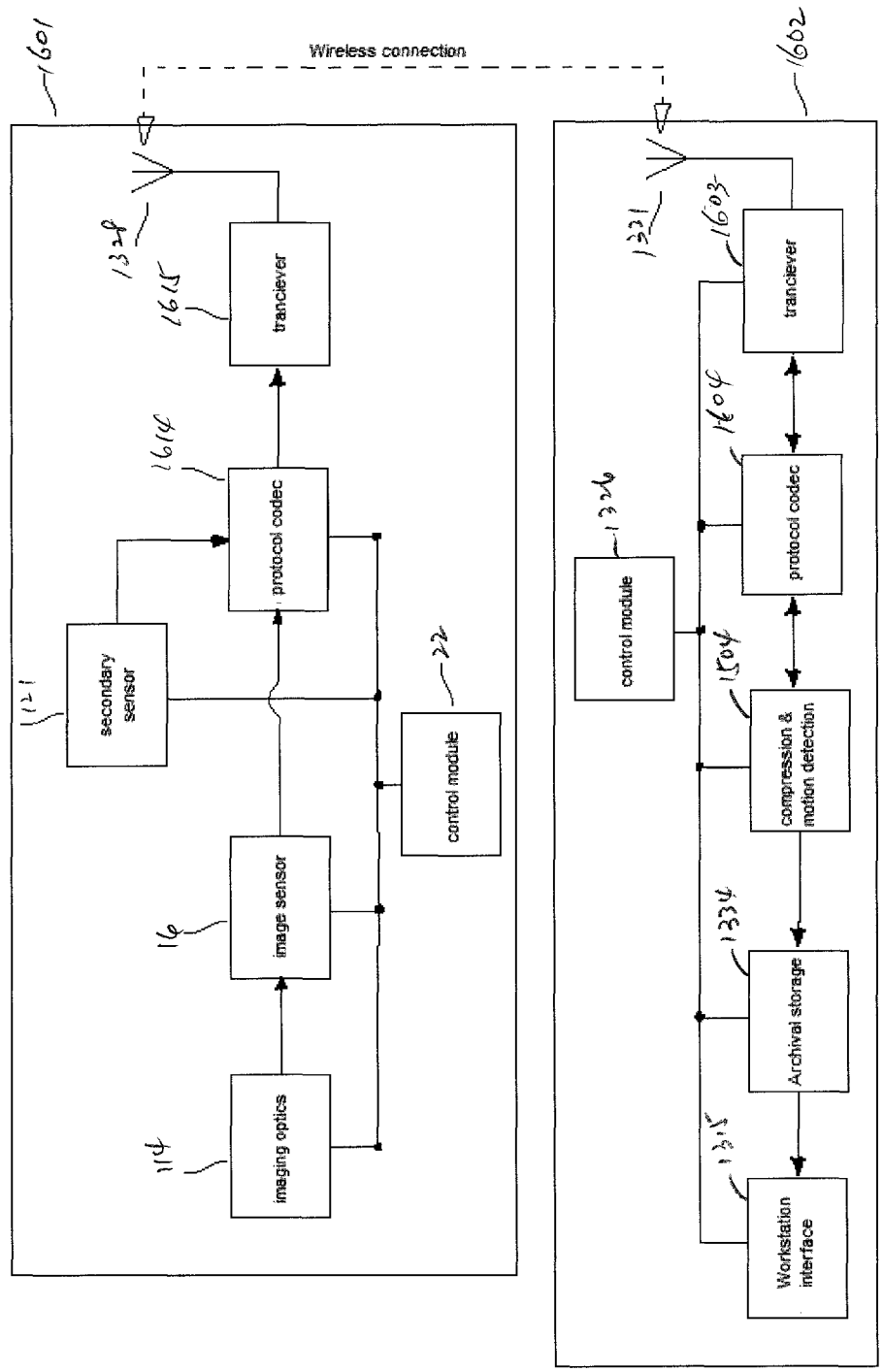
FIG. 16 is a functional block diagram of information flow in implementation 1600 during capsule camera operation in capsule system 02.

Alternatively, using bidirectional communication, the capsule and the base station may interact to allow the base station to control some of the functions in the capsule. For example, the base station may control the frequency at which the capsule captures images. When the base station detects motion in the captured images, the base station may send a message to the capsule to increase the frequency of image capture. Alternatively, the capsule may transmit a subset of a sequence of images, and if the base station detects motion in this subset, the base station may direct the capsule to transmit all or some of the images accumulated in the capsule. All of these functions would reduce the amount of data transmitted, thereby reducing the power requirement in the capsule. To allow interaction, the transmitter in the capsule and the receiver in the base station are replaced by transceivers. FIG. 16 shows implementation 1600, including capsule module 1601 and base station 1602, that provides the bidirectional communication between the capsule module and the base station. Capsule module 1601 and base station 1602 of FIG. 16 are substantially the same as capsule module 1501 and base station 1502 of FIG. 15, except that protocol encoder 1320 and transmitter 1326 in capsule module 1501 is replaced by protocol encoder-decoder ("codec") 1614 and transceiver 1615 in capsule module 1601, respectively. Similarly, receiver 1332 and protocol decoder 1333 in base station 1502 are replaced by transceiver 1603 and protocol codec 1604 in base station 1602, respectively. To save power, the receiver portion in transceiver 1615 need be on only during a window when the capsule expects a message from the base station (e.g., after the capsule sends a subset of the accumulated image).

Figure 17:
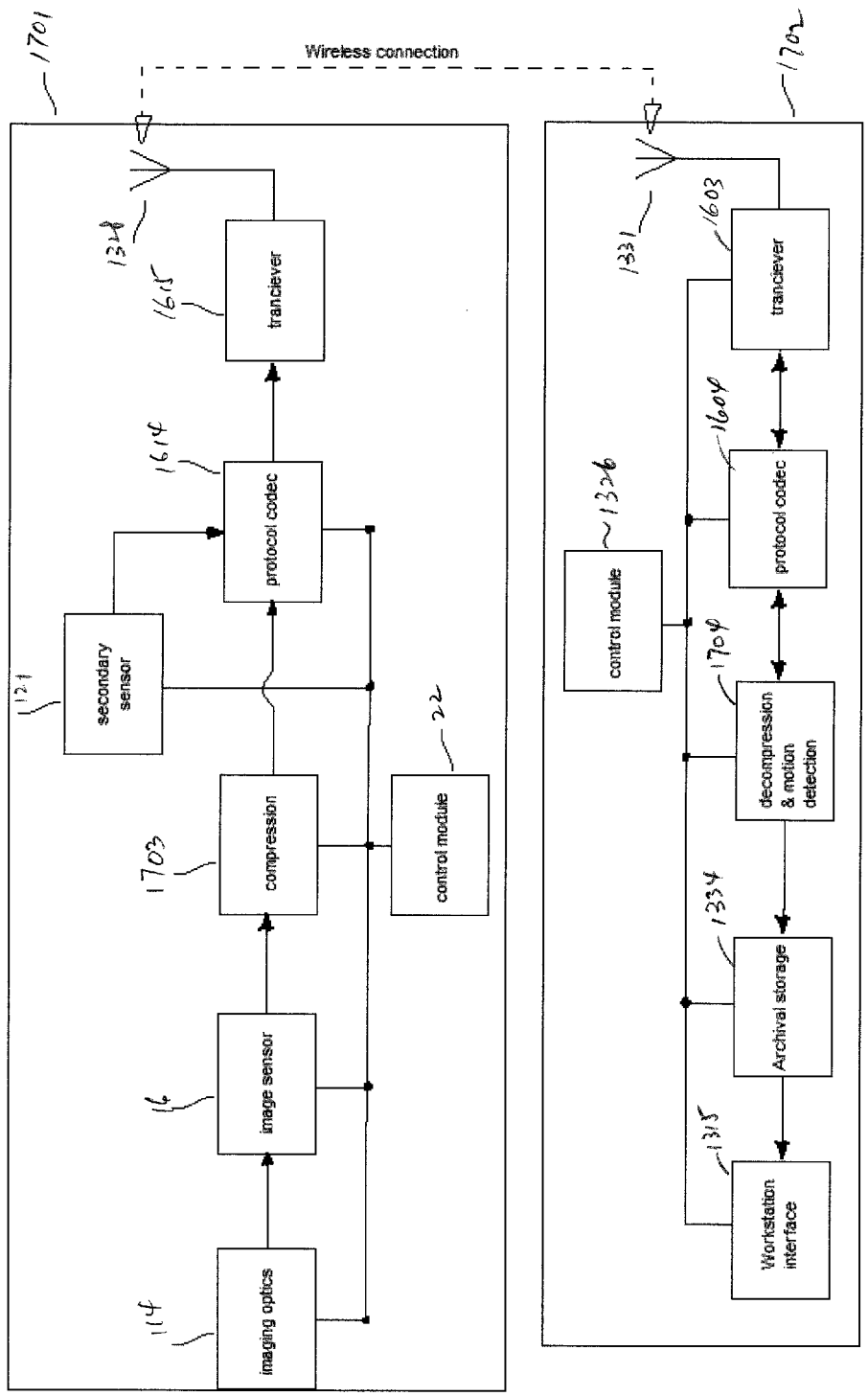
FIG. 17 is a functional block diagram of information flow in implementation 1700 during capsule camera operation in capsule system 02.

As mentioned above, there is an advantage in using a different resolution or compression ratio for the portion of the image used in motion detection than the resolution or compression ratio in storage. FIG. 17 shows implementation 1700, in which the transmitted images may be compressed under a different compression ratio than the compression ratio used in storage, according to one embodiment of the present invention. Capsule module 1701 and base station 1702 of FIG. 17 are substantially the same as capsule module 1601 and base station 1602 of FIG. 16, except that compression engine 1703 is provided in capsule module 1701 to allow images captured in image sensor 16 to be compressed before being provided to protocol codec 1614 to be processed for transmission. Similarly, decompression and motion detection module 1704 provides the required decompression and motion detection processing.

The above detailed description illustrates the specific embodiments of the present invention and is not intended to be limiting. Numerous modifications and variations within the scope of the invention are possible. The present invention is set forth in the following claims.

We claim:
1. A capsule camera apparatus, comprising:
a housing adapted to be swallowed;
a light source within the housing;
a camera within the housing for capturing a first digital image and a second digital image of a scene illuminated by the light source;
a processing circuit within the housing that processes the first digital image and the second digital image, at least a portion of each digital image having a higher resolution than the remainder of that digital image;
a motion detector within the housing that detects a motion based on a difference between the higher resolution portion of the first digital image provided in a first partial frame buffer and the higher resolution portion of the second digital image provided in a partial frame buffer; and
a motion evaluator within the housing that designates the second digital image for further processing based on a metric on the motion.

2. A capsule camera apparatus as in claim 1, wherein the motion evaluator designates the second digital image to be deleted.

3. A capsule camera apparatus as in claim 1, further comprising an archival storage device, wherein the motion evaluator designates the second digital image to be stored into the archival storage device.

4. A capsule camera apparatus as in claim 3, further comprising a register for storing the metric, the register being accessible by the motion evaluator during operation and being initialized with a value provided in the archival storage device.

5. A capsule camera apparatus as in claim 3, further comprising a register for storing the metric, the register being accessible by the motion evaluator during operation and being updated according to free space available in the archival storage device.

6. A capsule camera apparatus as in claim 3, wherein the archival storage device comprises a semiconductor memory device.

7. A capsule camera apparatus as in claim 6, wherein the semiconductor memory device comprises a flash memory device.

8. A capsule camera apparatus as in claim 3, further comprising an output port for accessing the archival storage device.

9. A capsule camera apparatus as in claim 8, wherein the output port is accessed through a connector.

10. A capsule camera apparatus as in claim 8, wherein the output port is accessed at a feed-through on the housing.

11. A capsule camera apparatus as in claim 8, wherein the capsule is capable of receiving power from an external power source.

12. A capsule camera apparatus as in claim 1, wherein a portion of the first digital image is stored in a first partial frame buffer and a portion of the second digital image is stored in a second partial frame buffer and the motion evaluator determines which of the first and second partial frame buffers is to be overwritten by a third digital image according to the motion detected.

13. A capsule camera apparatus as in claim 1, wherein the motion detector computes motion vectors between a portion of the first digital image and a portion of the second digital image.

14. A capsule camera apparatus as in claim 1, wherein the motion detector computes average absolute differences between corresponding portions of the first digital image and the second digital image.

15. A capsule camera apparatus as in claim 14, wherein the metric depends on a variance computed from the average absolute differences.

16. A capsule camera apparatus as in claim 1, wherein the motion detector computes for the first digital image and the second digital image each a center-of-mass.

17. A capsule camera apparatus as in claim 16, wherein the metric depends on a difference between the centers-of-mass computed.

18. A capsule camera apparatus as in claim 1, further comprising one or more sensors for detecting one or more environmental parameters.

19. A capsule camera apparatus as in claim 1, further comprising a transmitter within the housing for transmitting data over a wireless link.

20. A capsule camera apparatus as in claim 19, wherein the motion evaluator causes the designated digital image to be transmitted over the wireless link.

21. A capsule camera apparatus as in claim 19, further comprising a protocol encoder for encoding data for transmission by the transmitter.

22. A capsule camera apparatus as in claim 19, wherein the capsule camera apparatus is designed to communicate with a base station, the base station comprising a receiver that receives data over the wireless link.

23. A capsule camera apparatus as in claim 22, wherein the base station further comprises an interface to a workstation.

24. A capsule camera apparatus as in claim 22, wherein the base station further comprises an archival storage system.

25. A capsule camera apparatus as in claim 22, further comprising a transmitter in the base station to allow bidirectional communication over the wireless link.

26. A capsule camera apparatus as in claim 25, further comprising a register for storing the metric, the register being accessible by the motion evaluator during operation and being initialized with a value provided over the wireless link.

27. A capsule camera apparatus as in claim 1, wherein the designated digital image is compressed using an image compression algorithm.

28. A capsule camera apparatus as in claim 27, wherein the first compression ratio is provided to the designated digital image when operated upon by the motion detector which is different from a second compression ratio provided to the designated digital image for further processing.

29. A capsule camera apparatus as in claim 1, further comprising a register for storing the metric, the register being accessible by the motion evaluator during operation.

30. A capsule camera apparatus as in claim 1, wherein the metric is designed to prefer motion in the forward direction along the length of the GI tract.

31. A capsule camera apparatus as in claim 1, wherein the motion detector accords little or no weight to retrograde motion.

32. A capsule camera apparatus, comprising:
a housing adapted to be swallowed, said housing enclosing:
  a light source;
  a camera for capturing a first digital image and a second digital image of a scene illuminated by the light source;
  a motion detector that detects a motion based on computed motion vectors each representing a difference between a portion of the first digital image provided in a first partial frame buffer and a portion of the second digital image provided in a partial frame buffer; and
  a motion evaluator that designates the second digital image for further processing, based on a metric on the detected motion, wherein the metric has a value that depends on (i) a count of zero-valued motion vectors, (ii) an average of the absolute differences between corresponding portions of the first digital image and the second digital image, or (iii) a variance computed from the average absolute differences.

33. A method for operating a capsule camera, comprising:
providing a housing adapted to be swallowed;
providing a light source and a camera within the housing;
capturing a first digital image and a second digital image of a scene illuminated by the light source;
processing, within the housing, the first digital image and the second digital image, at least a portion of each digital image having a higher resolution than the remainder of that digital image;
detecting, within the housing, a motion based on a difference between the higher resolution portion of the first digital image provided in a first partial frame buffer and the higher resolution portion of the second digital image provided in a second partial frame buffer, and
evaluating, within the housing, the motion to designate the second digital image for further processing based on a metric on the motion.

34. A method as in claim 33, wherein the motion evaluator designates the second digital image to be deleted.

35. A method as in claim 33, wherein the evaluating comprises designating the second digital image to be stored into an archival storage device.

36. A method as in claim 35, further comprising accessing the archival storage device through an output port.

37. A method as in claim 36, wherein the output port is accessed through a connector.

38. A method as in claim 36, wherein the output port is accessed at a feed-through on the housing.

39. A method as in claim 36, wherein capsule receives power from an external power source.

40. A method as in claim 35, further comprising storing the metric in a register, the register being accessible by the motion evaluator during operation and being initialized with a value provided in the archival storage device.

41. A method as in claim 35, further comprising storing the metric in a register, the register being accessible by the motion evaluator during operation and being updated according to free space available in the archival storage device.

42. A method as in claim 33, wherein the archival storage device comprises a semiconductor memory device.

43. A method as in claim 42, wherein the semiconductor memory device comprises a flash memory device.

44. A method as in claim 33, wherein a portion of the first digital image is stored in a first partial frame buffer and a portion of the second digital image is stored in a second partial frame buffer and the evaluating determines which of the first and second partial frame buffers is to be overwritten by a third digital image according to the motion detected.

45. A method as in claim 33, wherein the detecting comprises computing motion vectors between a portion of the first digital image and a portion of the second digital image.

46. A method as in claim 33, wherein the detecting comprises computing average absolute differences between corresponding portions of the first digital image and the second digital image.

47. A method as in claim 46, wherein the metric depends on a variance computed from the average absolute differences.

48. A method as in claim 33, wherein the detecting comprises computing for the first digital image and the second digital image each a center-of-mass.

49. A method as in claim 48, wherein the metric depends on a difference between the centers-of-mass computed.

50. A method as in claim 33, further comprising providing one or more sensors for detecting one or more environmental parameters.

51. A method as in claim 33, further comprising providing a transmitter within the housing for transmitting data over a wireless link.

52. A method as in claim 51, wherein the evaluating designates the second digital image to be transmitted over the wireless link.

53. A method as in claim 51, further comprising encoding in a protocol encoder the data to be transmitted.

54. A method as in claim 51, further comprising providing a base station that receives data over the wireless link.

55. A method as in claim 54, further comprising providing an interface to a workstation in the base station.

56. A method as in claim 54, further comprising providing an archival storage in the base station.

57. A method as in claim 54, further comprising transmitting from the base station in bidirectional communication over the wireless link.

58. A method as in claim 57, further comprising storing the metric in a register, the register being accessible by the motion evaluator during operation and being initialized with a value provided over the wireless link.

59. A method as in claim 33, further comprising compressing the designated digital image using an image compression algorithm.

60. A method as in claim 59, wherein the first compression ratio is provided to the designated digital image when operated upon by the motion detector which is different from a second compression ratio provided to the designated digital image for further processing.

61. A method as in claim 33, further comprising a register for storing the metric, the register being accessible by the motion evaluator during operation.

62. A method as in claim 33, wherein the metric is designed to prefer motion in the forward direction along the length of the GI tract.

63. A method as in claim 33, wherein the motion detector accords little or no weight to retrograde motion.

64. A method for operating a capsule camera, comprising:
providing a housing adapted to be swallowed;
providing a light source, a camera and a motion circuit within the housing;
capturing a first digital image and a second digital image of a scene, illuminated by the light source, with the camera;
detecting a motion with the motion circuit based on computed motion vectors each representing a difference between a portion of the first digital image provided in a first partial frame buffer and a portion of the second digital image provided in a second partial frame buffer; and
evaluating the motion with the motion circuit to designate the second digital image for further processing, based on a metric on the detected motion, wherein the metric has a value which depends on (i) a count of zero-valued motion vectors, (ii) an average of the absolute differences between corresponding portions of the first digital image and the second digital image, or (iii) a variance computed from the average absolute differences.

65. A capsule camera apparatus, comprising:
a housing adapted to be swallowed;
a light source within the housing;
a camera within the housing for capturing a first digital image and a second digital image of a scene illuminated by the light source;
means for processing, within the housing, the first digital image and the second digital image, at least a portion of each digital image having a higher resolution than the remainder of that digital image;
means for detecting, within the housing, a motion using a difference between the higher resolution portion of the first digital image provided in a first partial frame buffer and the higher resolution portion of the second digital image provided in a second partial frame buffer, and
means for designating, within the housing, the second digital image for further processing based on a metric on the motion.

66. A capsule camera apparatus as in claim 65 further comprising an archival storage, wherein the deposition comprises storing the second digital image in the archival storage.

67. A capsule camera apparatus as in claim 65, wherein means for transmitting the designated digital image over a wireless link.

68. A capsule camera apparatus, comprising:
a housing adapted to be swallowed;
a light source within the housing;
a camera within the housing for capturing a digital image of a scene illuminated by the light source;
a processing circuit, within the housing, that processes the captured image to provide a processed digital image having at least one portion having a higher resolution than the remainder of the processed digital image;
a motion detection circuit, within the housing, that detects motion between the processed images corresponding to images captured at different times and selects the processed digital images based on a metric on motion;
an archival storage device for storing the selected digital images; and
an output port for retrieving the stored digital image from the archival storage system.

69. A capsule camera apparatus as in claim 68, further comprising an image selection circuit for designating digital images to be stored into the archival storage device.

70. A capsule camera apparatus as in claim 68, wherein the archival storage device comprises a semiconductor memory device.

71. A capsule camera apparatus as in claim 70, wherein the semiconductor memory device comprises a flash memory device.

72. A capsule camera apparatus as in claim 68, wherein the output port is accessed through a connector.

73. A capsule camera apparatus as in claim 68, wherein the output port is accessed at a feed-through on the housing.

74. A capsule camera apparatus as in claim 68, wherein the capsule is capable of receiving power from an external power source.

75. A method for providing a capsule camera apparatus, comprising:
providing a housing adapted to be swallowed;
providing a light source within the housing;
using a camera within the housing, capturing a digital image of a scene illuminated by the light source;
processing, within the housing, the captured image to provide a processed digital image having at least one portion having a higher resolution than the remainder of the processed digital image;
detecting, within the housing, motion between the processed images corresponding to images captured at different times and selecting the processed digital images based on a metric on motion;
storing the selected digital image in an archival storage device; and
retrieving the selected digital image from the archival storage system through an output port.

76. A method as in claim 75, further comprising providing an image selection circuit for designating digital images to be stored into the archival storage device.

77. A method as in claim 75, wherein the archival storage device comprises a semiconductor memory device.

78. A method as in claim 77, wherein the semiconductor memory device comprises a flash memory device.

79. A method as in claim 75, wherein the output port is accessed through a connector.

80. A method as in claim 75, wherein the output port is accessed at a feed-through on the housing.

81. A method as in claim 75, wherein the capsule is capable of receiving power from an external power source.

* * * * *